(12) United States Patent
Spiegel et al.

(10) Patent No.: US 11,373,545 B2
(45) Date of Patent: Jun. 28, 2022

(54) METHODS AND KITS FOR IDENTIFYING FOOD SENSITIVITIES AND INTOLERANCES

(71) Applicants: CEDARS-SINAI MEDICAL CENTER, Los Angeles, CA (US); The Regents of the University of Michigan, Ann Arbor, MI (US)

(72) Inventors: Brennan Spiegel, Los Angeles, CA (US); William D. Chey, Ann Arbor, MI (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 16/993,919

(22) Filed: Aug. 14, 2020

(65) Prior Publication Data

US 2021/0065580 A1 Mar. 4, 2021

Related U.S. Application Data

(62) Division of application No. 15/323,857, filed as application No. PCT/US2015/039817 on Jul. 9, 2015, now Pat. No. 10,810,904.

(Continued)

(51) Int. Cl.
*G09B 19/00* (2006.01)
*G06Q 30/02* (2012.01)
(Continued)

(52) U.S. Cl.
CPC ..... *G09B 19/0092* (2013.01); *G06Q 30/0282* (2013.01); *G09B 7/10* (2013.01);
(Continued)

(58) Field of Classification Search
CPC . G09B 19/0092; G06F 19/3475; A61B 5/411; A61K 49/0004; G61H 20/60
See application file for complete search history.

(56) References Cited

U.S. PATENT DOCUMENTS

| 5,639,471 A | 6/1997 | Chait et al. |
| 8,647,267 B1 | 2/2014 | Long |
| (Continued) | | |

FOREIGN PATENT DOCUMENTS

| AU | 2015287717 A1 | 2/2017 |
| CA | 2954641 A1 | 1/2016 |
| (Continued) | | |

OTHER PUBLICATIONS

PCT/US2015/039817 International Search Report and Written Opinion dated Dec. 4, 2015; 10 pages.

(Continued)

*Primary Examiner* — Omkar A Deodhar
(74) *Attorney, Agent, or Firm* — Nixon Peabody LLP

(57) ABSTRACT

Described herein are kits and methods for identifying the likelihood of having a food sensitivity or intolerance, and determining dietary modifications accordingly. For example, the likelihood of having sensitivities, intolerances or allergies to gluten, lactose, FODMAPs and others tested and calculated. Additionally, diet modifications can be determined according to the likelihood of particular sensitivities, and the effectiveness of diet modifications can be evaluated by monitoring of meals and subsequent symptoms, and evaluating the monitoring information. Through application of the methods herein, dietary intake and symptom data may be collected and aggregated to evaluate the effect or desirability of particular foods on a population of interest.

20 Claims, 27 Drawing Sheets

Related U.S. Application Data

(60) Provisional application No. 62/022,378, filed on Jul. 9, 2014.

(51) Int. Cl.
*G16H 20/60* (2018.01)
*G16H 10/20* (2018.01)
*G16H 15/00* (2018.01)
*G09B 7/10* (2006.01)

(52) U.S. Cl.
CPC .............. *G16H 10/20* (2018.01); *G16H 15/00* (2018.01); *G16H 20/60* (2018.01)

(56) References Cited

U.S. PATENT DOCUMENTS

| | | |
|---|---|---|
| 10,810,904 B2 | 10/2020 | Spiegel et al. |
| 2006/0189853 A1 | 8/2006 | Brown |
| 2008/0220450 A1 | 9/2008 | Harding |
| 2009/0298021 A1 | 12/2009 | Black et al. |
| 2010/0145725 A1 | 6/2010 | Alferness et al. |
| 2010/0235184 A1 | 9/2010 | Firminger et al. |
| 2011/0300519 A1* | 12/2011 | Lemieux ............ G09B 19/0092 434/127 |
| 2012/0173269 A1 | 7/2012 | Omidi |
| 2013/0261183 A1 | 10/2013 | Bhagat |
| 2014/0122104 A1 | 5/2014 | Van Halteren et al. |
| 2017/0148349 A1 | 5/2017 | Spiegel et al. |

FOREIGN PATENT DOCUMENTS

| | | |
|---|---|---|
| EP | 3167339 A1 | 5/2017 |
| WO | 2016007793 A1 | 1/2016 |

OTHER PUBLICATIONS

Karen Cropper, Food Diary Apps—For Food Allergy Elimination Diet, 2014, retrieved from internet on May 6, 2019, <URL:https://karencropper.wordpress.com/2014/02/08/food-diary-apps-for-food-allergy-elimination-diet/> published on Mar. 11, 2014 as per Wayback Machine, 5 Pages.

Extended European Search Report of EP 15818193.3, dated Oct. 25, 2017, 7 Pages.

* cited by examiner

N=1 Crossover Trial

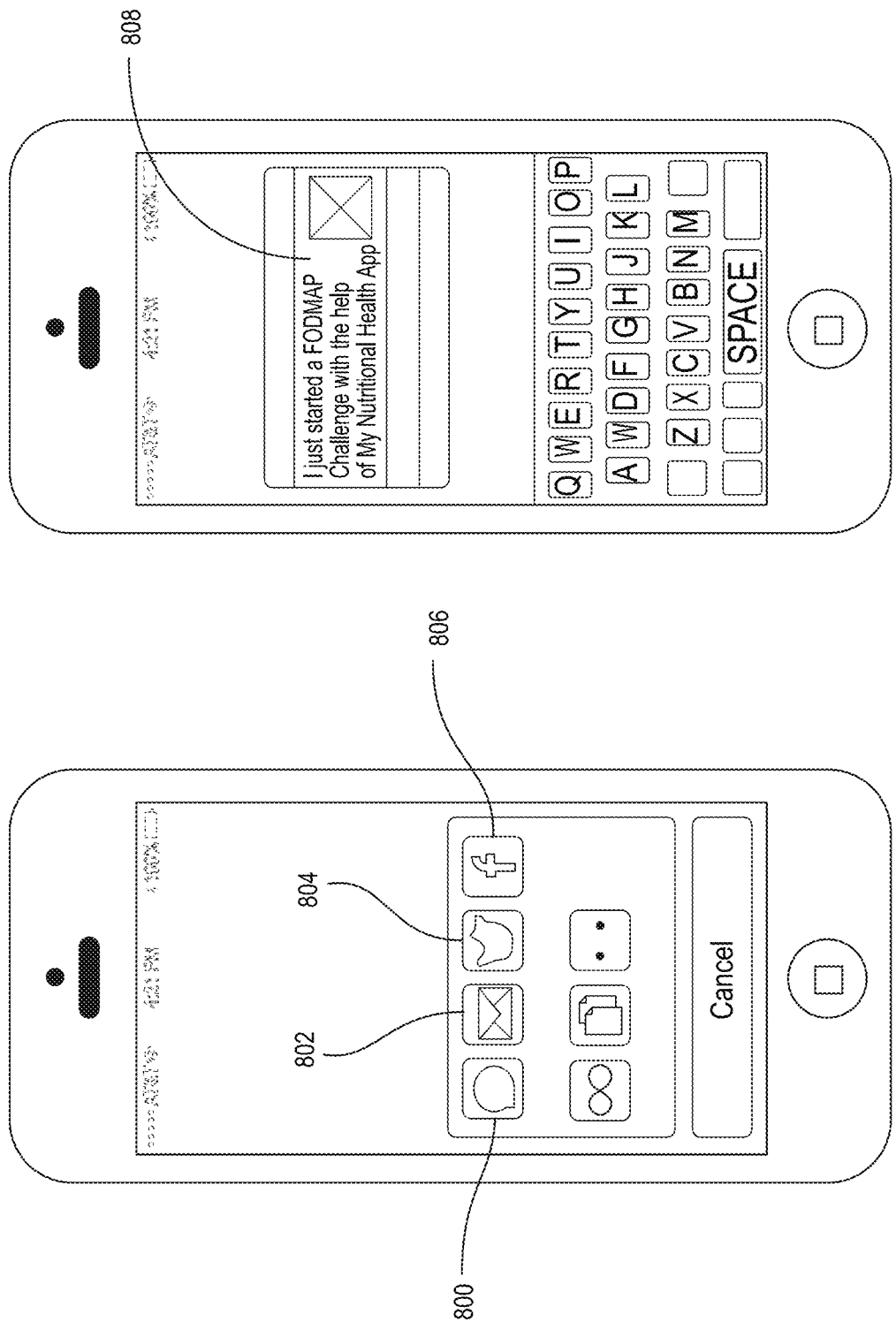

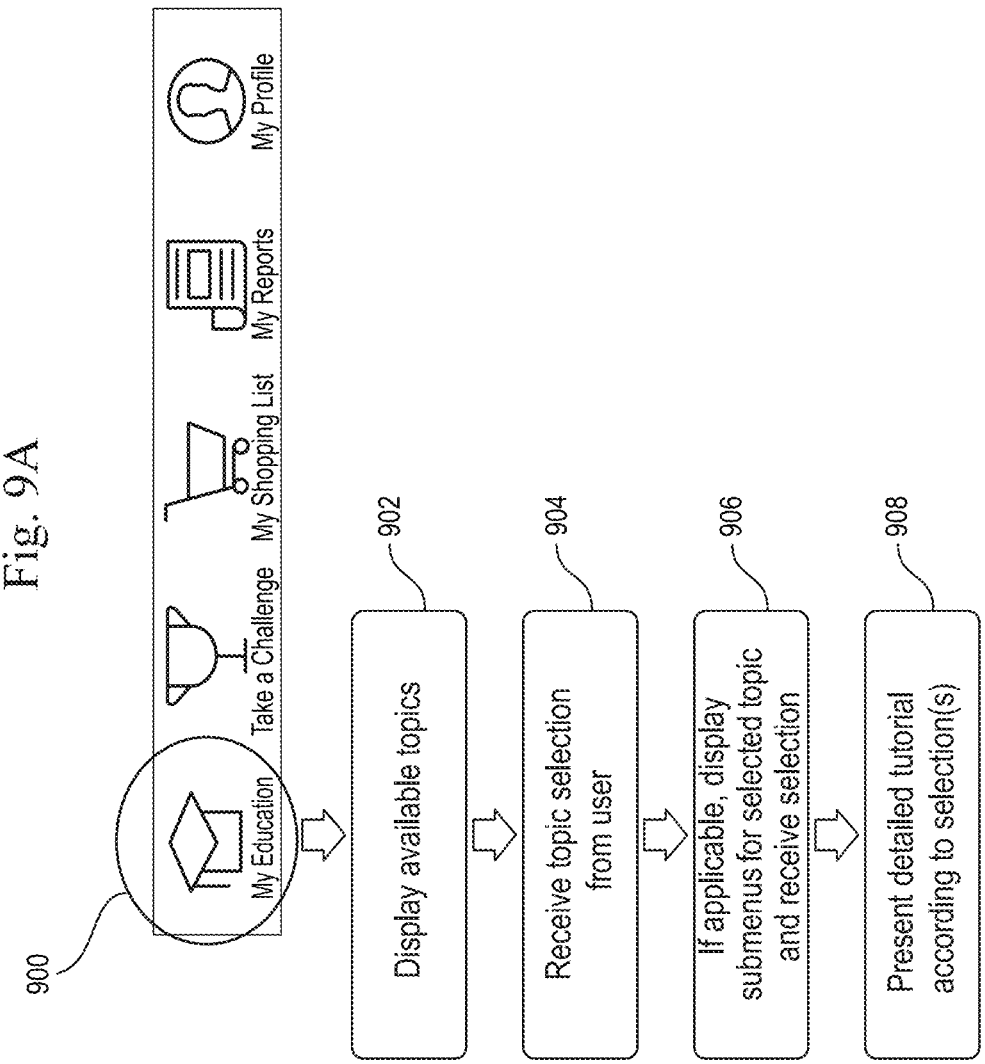

Fig. 10F

Start Date

Select your start date.
It is best to start at the beginning of the day.

Start    Sept 12, 2014 8:00 AM

Wed Sep 10   6   50
Thu Sep 11   7   55
Today        8   00   AM
Sat Sep 13   9   05   PM
Sun Sep 14   10  10

Next

<Back   Preferences

We understand that some people have meal restrictions or preferences.
Please select anything that you DO NOT wish to have.

🔍 Search

☐ [Item Name]
☐ [Item Name]
☐ [Item Name]
☐ [Item Name]

Next

1042

1044

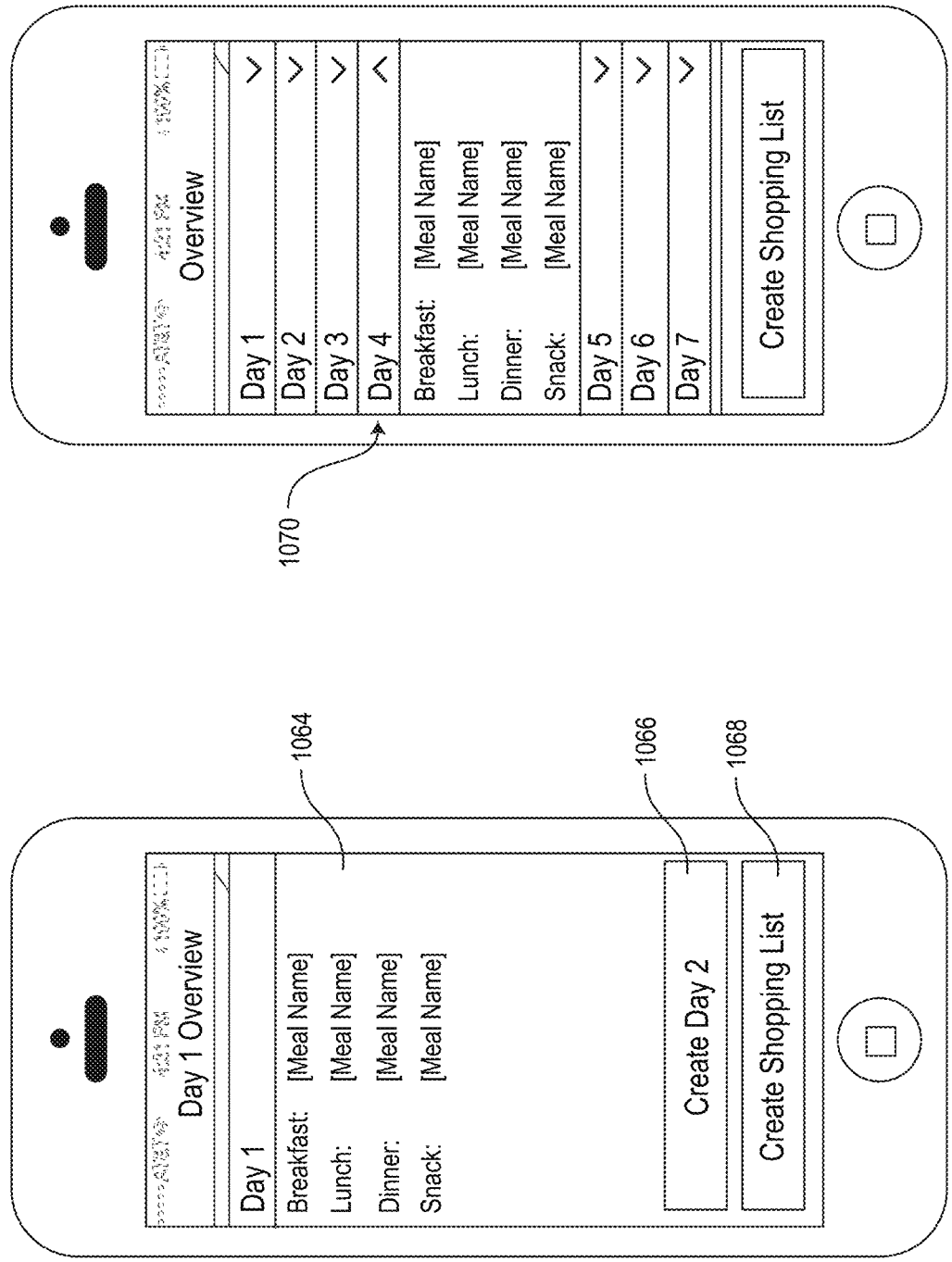

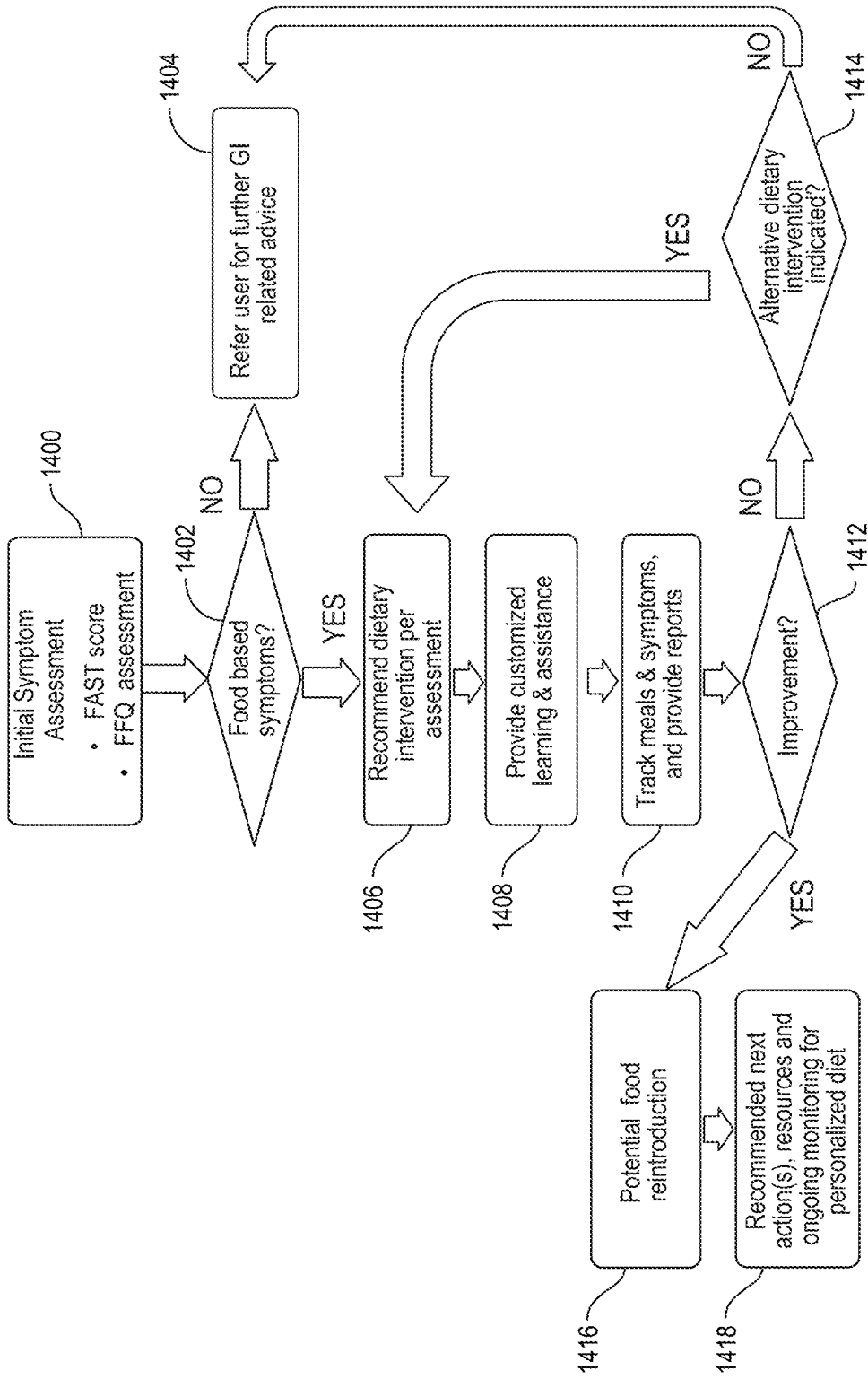

METHODS AND KITS FOR IDENTIFYING FOOD SENSITIVITIES AND INTOLERANCES

CROSS-REFERENCE TO RELATED APPLICATIONS

This application is a Divisional of U.S. application Ser. No. 15/323,857, filed Jan. 4, 2017, which is a National Phase of International Application No. PCT/US2015/039817 filed Jul. 9, 2015, which designated the U.S. and that International Application was published under PCT Article 21(2) in English, which include a claim of priority under 35 U.S.C. § 119(e) to U.S. provisional patent application No. 62/022,378 filed Jul. 9, 2014, the entirety of which is hereby incorporated by reference.

FIELD OF INVENTION

This invention relates to the identification of food sensitivities and intolerances such as gluten sensitivity, lactose intolerance and FODMAPs sensitivity, and methods for performing and assessing dietary modifications relating thereto, including but not limited to using standardized meal sets for these purposes.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

In the absence of true food allergies or specific food related diseases like Celiac Disease, persons who develop gastrointestinal symptoms like abdominal pain, cramping, bloating, flatulence, or altered bowel habits or non-GI symptoms like fatigue, headache or joint pain after eating specific foods are thought to suffer from a "food sensitivity" or "food intolerance". Food sensitivities and intolerances are highly prevalent in the general population, including intolerance of gluten, lactose, and "FODMAPs" (fermentable oligosaccharides, disaccharides, monosaccharaides, and polyols). Although many people suspect they have sensitivities to or are intolerant of certain foods, there is no specific diagnostic test or even a standardized method to identify a food sensitivity or intolerance. Many patients undergo expensive and specialized testing to exclude a food allergy, or consultation with medical specialists or dieticians using detailed food diaries coupled with extensive trial and error to determine if they have a food sensitivity or intolerance. Given the high prevalence and importance of food sensitivities and intolerances, there is an unmet need and large demand to develop an evidence-based, inexpensive, and widely available method for determining if someone has a food sensitivity or intolerance.

BRIEF DESCRIPTION OF THE FIGURES

Exemplary embodiments are illustrated in referenced figures. It is intended that the embodiments and figures disclosed herein are to be considered illustrative rather than restrictive.

FIG. 8A-8B illustrate application features for social sharing, according to an embodiment of the present disclosure.

FIG. 14 illustrates a method for applying the MNH capabilities to determine, implement, and evaluate a dietary intervention, according to an embodiment of the present disclosure.

Figure 1:
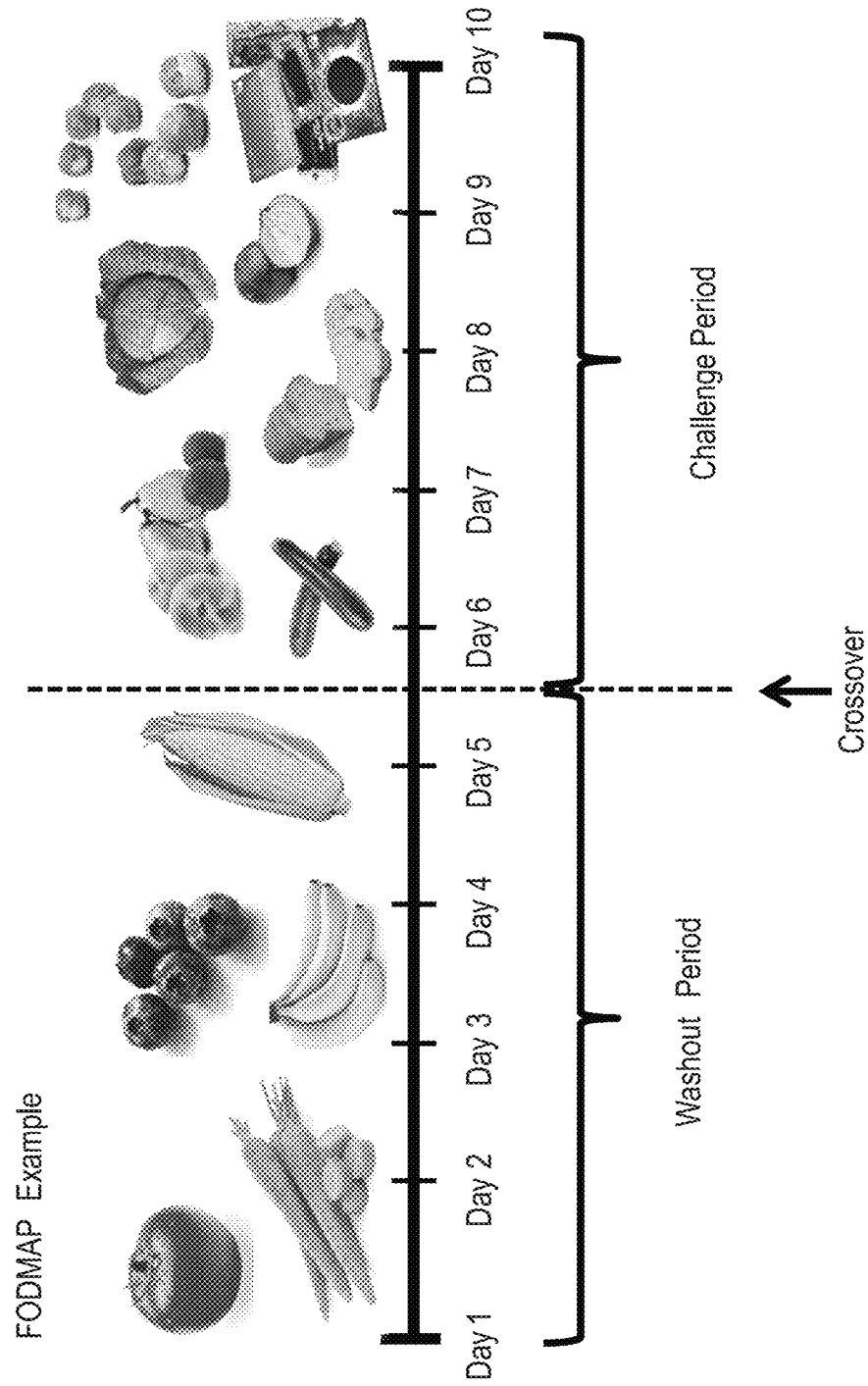
FIG. 1 depicts, in accordance with various embodiments of the present invention, an exemplary test period for FODMAPs.
Figure 2:
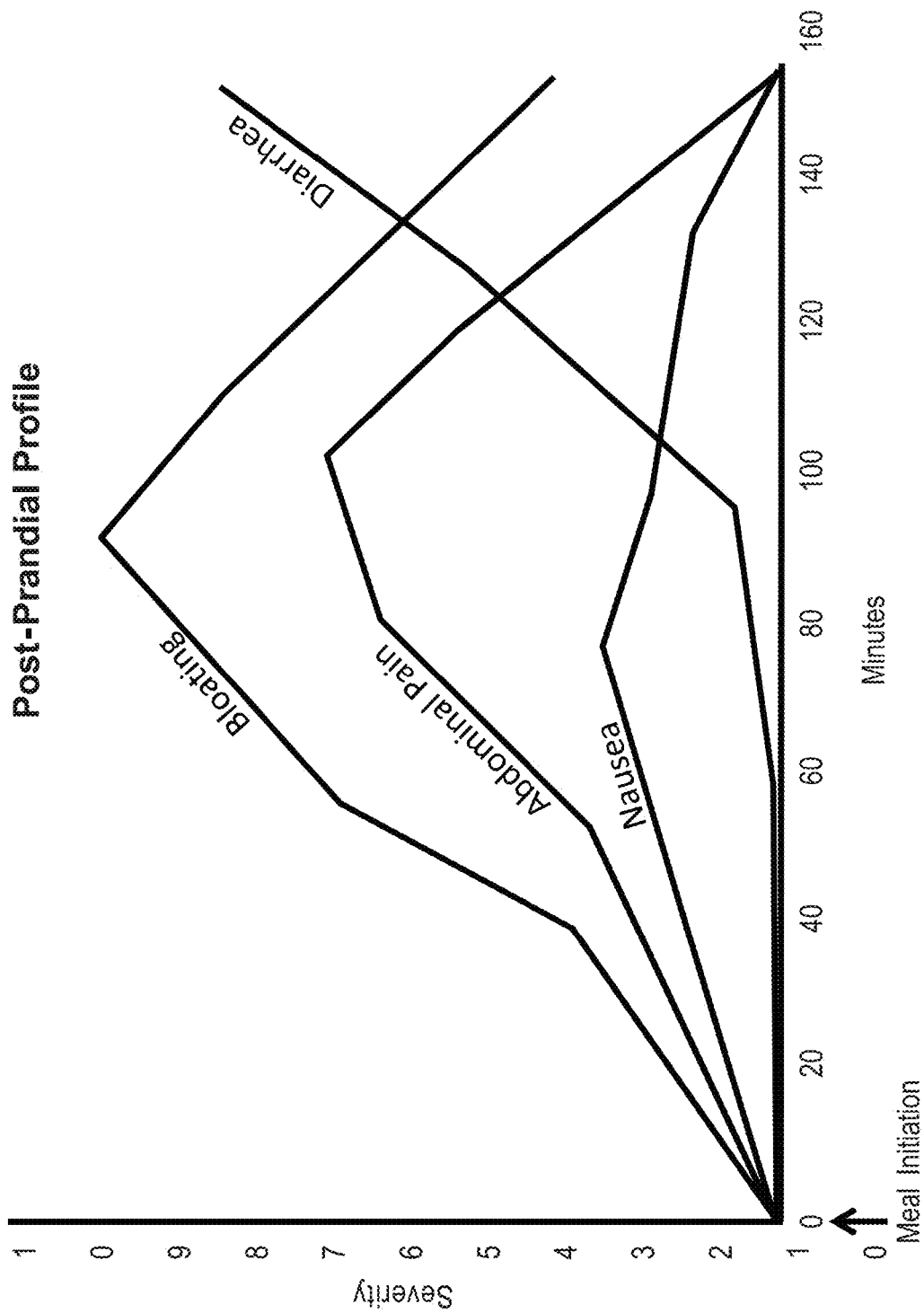
FIG. 2 depicts, in accordance with various embodiments of the present invention, an exemplary post-prandial profile.
Figure 3:
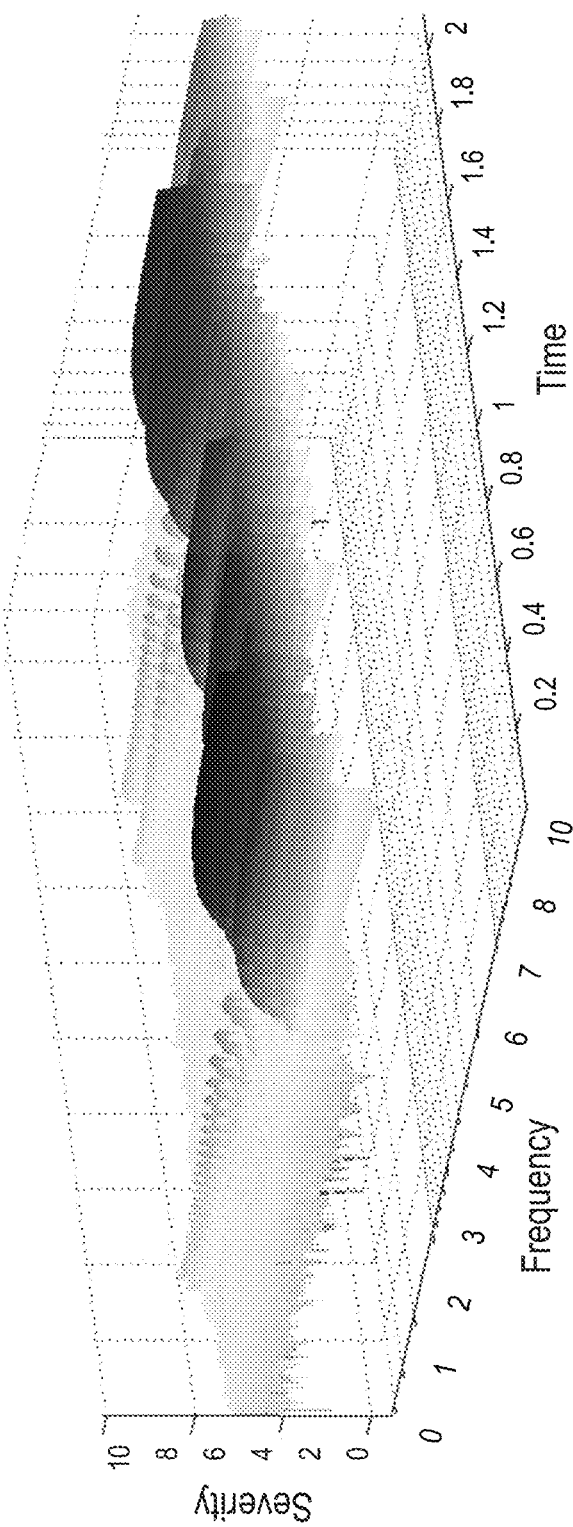
FIG. 3 depicts, in accordance with various embodiments of the present invention, an exemplary washout period FAST profile.
Figure 4:
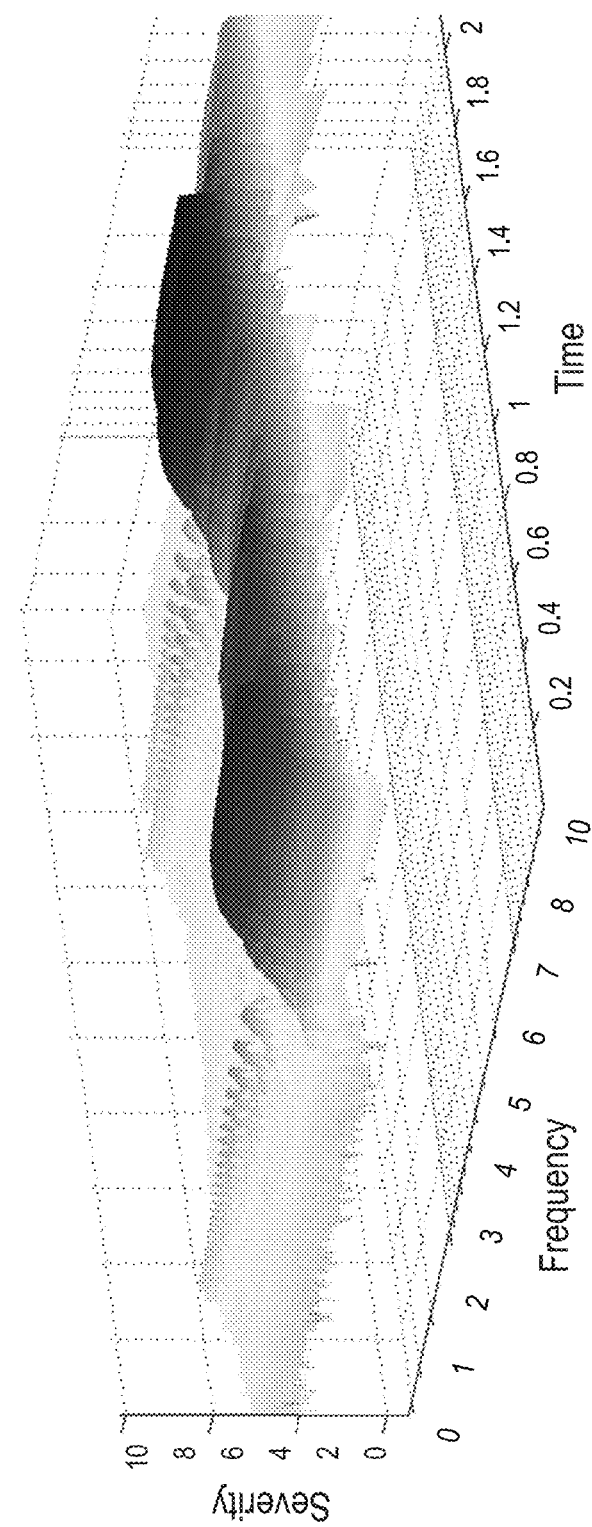
FIG. 4 depicts, in accordance with various embodiments of the present invention, an exemplary challenge period FAST profile.
Figure 5:
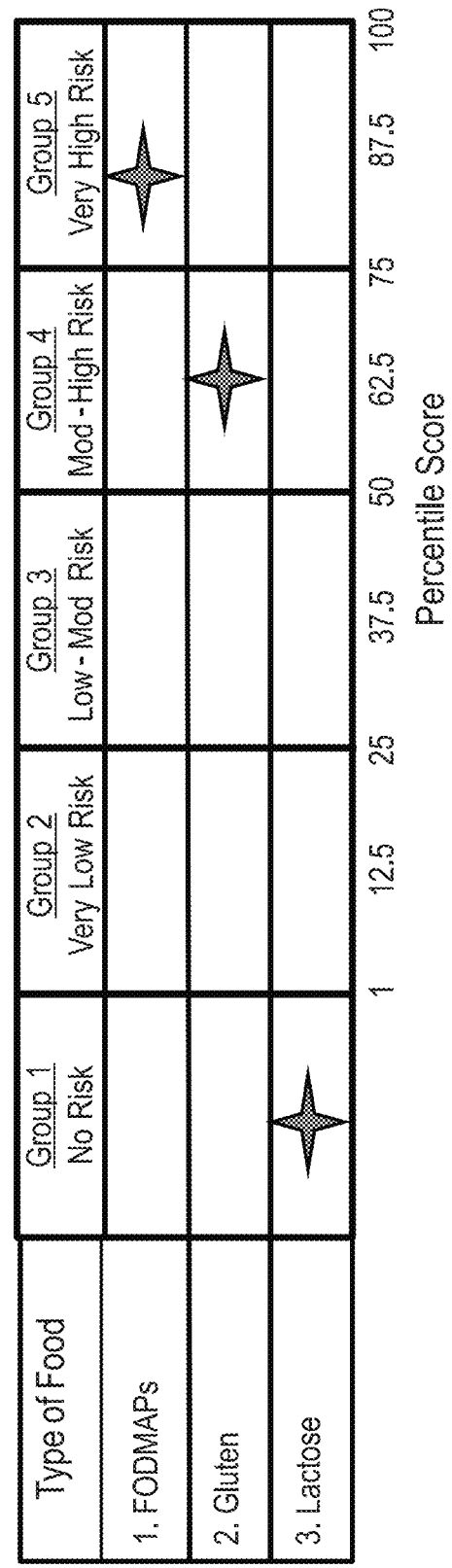
FIG. 5 depicts, in accordance with various embodiments of the present invention, an exemplary food and symptom tracker (FAST) report.

While the disclosure is susceptible of embodiment in many different forms, there is shown in the drawings and will herein be described in detail preferred embodiments with the understanding that the present disclosure is to be considered as an exemplification of the principles of the invention and is not intended to limit the broad aspect of the invention to the embodiments illustrated.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described.

"Food sensitivity" as used herein refers to an unpleasant reaction to certain foods or constituents in certain foods; for example, reactions such as but not limited to gastrointestinal symptoms and extraintestinal symptoms. Examples of food sensitivities include but are not limited to gluten sensitivity and FODMAP sensitivity.

"Food intolerance" as used herein refers to a reaction when the body lacks a particular enzyme to digest the food or a constituent in the food. A non-limiting example of food intolerance is lactose intolerance. Examples of reactions that the body develops include but are not limited to gastrointestinal symptoms and extraintestinal symptoms.

One major issue involves the difficulties involved with accurately tracking food intake. But beyond the actual tracking of food, there is the tremendous amount of noise inherent in the data. One can try to create a series of scores that track food ingestion against symptom expression, then create normal distribution curves for how people physically respond to known ingestions, which is hard enough to do, but if the complexity of food tracking is added on top of that, coupled with the complexity of normal diets ranging widely from person-to-person, it becomes almost impossible to really measure these things.

There are many reasons that this may not work. Not just that the food tracking may not work (which is an important but solvable issue), or that people will not really want to track their dietary intake carefully, or that they will be accurate in their dietary intake tracking, but that even if they do all of that correctly and with appropriate technologies, that their data will still be diverse and extremely difficult to interpret in almost all cases. So, tracking a range of common symptoms, from GI symptoms to extra-intestinal symptoms like fatigue and headache, and linking them back to very imprecise data will yield very imprecise results.

The inventors have solved this issue, as described herein.

The way people typically figure things out in "real life" is to systematically eliminate specific dietary constituents, and then re-introduce them to see if they cause a problem. Described herein is a formalized version of that; a series of N=1 cross-over experiments with each individual user becoming their own control. Also described herein removes the need, completely, for tracking any meals on an application; it removes the intractable noise in usual meals that undermine effective measurement models; and it provides a standard stimulus that ties to a standard score. This also distinguishes it from existing applications in the art.

Described herein are kits and methods for quantifying dietary sensitivity using a standardized meal challenge and a mobile health application.

Kits

Various embodiments of the present invention describe a kit for determining the likelihood of having a food sensitivity or intolerance, comprising: a standardized meal set comprising two subsets of standardized test meals and instructions for consuming the standardized meal set for a testing period.

One subset of standardized test meals comprises meals for an "Elimination" phase; the other, optional, subset of standardized test meals comprises meals for a "Challenge" phase for purposes of identifying any of a number of different types of specific food sensitivities or intolerances (for example but not limited to gluten, lactose, fermentable carbohydrates, fats, proteins, or chemicals).

During the Elimination phase, meals (e.g., breakfast, lunch, dinner and snacks) lacking the culprit dietary constituent suspected to be causing the food sensitivity or food intolerance will be given for a pre-specified period of time. In the Challenge phase, a set of meals enriched with the culprit dietary constituent suspected of causing the food sensitivity will be provided for a pre-specified period of time. The duration of the challenge will be sufficient to identify the food sensitivity or food intolerance. In an embodiment, the Challenge phase is optional. Meals will be nutritionally balanced and calorie appropriate based upon the patient's body mass index and activity level.

In further embodiments, the kit further comprises adjunctive instructions relating to the use of the standardized meal. For example, the adjunctive instructions can be instructions on liquid ingestions; instructions on medications and supplements the subject may be taking, instructions regarding consumption of alcohol, instructions on daily activity, instructions regarding stress levels (for example, the subject should avoid parts or all of the testing period if he or she is under abnormal amounts of stress).

In various embodiments, the kit comprises instructions for the subject to consume the meal set of the elimination period before the meal set of the challenge period. In other embodiments, the kit comprises instructions for the subject to consume the meal set of the challenge period before the meal set of the elimination period. In still other embodiments, the kit comprises instructions for the subject to consume one meal set before the other meal set, but the subject is "blinded" to which meal set is the elimination period and which meal set is the challenge period. In these embodiments, there will be identifying information on the meal set that allows the test provider to have knowledge on which meal set corresponds to the elimination period and which meal set corresponds to the challenge period; however, the subject consuming the meal will not have the knowledge. For example, one set of meals can be marked "A" and one set is marked "B", wherein "A" corresponds to the elimination period and "B" corresponds to the challenge period. In another example, the kit can have a computer readable code or a serial number (which can comprise numbers, letters and/or symbols) that allows the provider to distinguish the two meal sets, and allow for the calculation of the FAST score.

In further embodiments, the kit further comprises a computer readable code that allows consumers to download a companion mobile health application for use in concert with the standardized meal set. In various embodiments, the computer readable code is a quick response (QR) code.

In other embodiments, the kit further comprises a web address or other identifying features that allows consumers to download a companion mobile health application for use in concert with the standardized meal set.

Standardized Meal Set

In various embodiments, a kit for determining the likelihood of having a gluten sensitivity or gluten allergy. Thus, the standardized meal set is configured for that determination. During the elimination period, the meals do not comprise gluten. In some embodiments, the meals in the elimination period also do not comprise lactose and/or FODMAPs. During the challenge period, the meals comprise gluten. In an embodiment the challenge period is optional. In some embodiments, the meals in the challenge period do not comprise lactose and/or FODMAPs. In some embodiments, the meals during the challenge period comprise varying amounts of gluten.

The meal set for the elimination period of gluten can be for a number of days that is sufficient for allowing gluten to be sufficiently removed from the body. For example, the elimination period can for about 2-14 days; for example, for 2, 3, 4, 5, 6, 7, 8, 9, 10, 11, 12, 13, or 14 days. In some embodiments, the elimination period can be for about 2-10 days. For some embodiments, the elimination period can be for about 2-7 days. For some embodiments, the elimination period can be for about 2-5 days. In certain embodiments, the elimination period can be about 14 days.

The meal set for the challenge period of gluten can be for a number of days that is sufficient for allowing the body to react to gluten. For example, the challenge period can for about 2-21 days; for example, for 2, 3, 4, 5, 6, 7, 8, 9, 10, 11, 12, 13, 14, 15, 16, 17, 18, 29, 20, or 21 days. In some embodiments, the challenge period can be for about 5-21 days. For some embodiments, the challenge period can be for about 7-14 days. For some embodiments, the challenge period can be for about 7, 10, or 14 days. In certain embodiments, the challenge period can be 7 days. In other embodiments, the challenge period can be 14 days.

In various embodiments, a kit for determining the likelihood of having lactose intolerance. Thus, the standardized meal set is configured for that determination. During the elimination period the meals do not comprise lactose. In some embodiments, the meals during the elimination period also do not comprise gluten or FODMAPs. During the challenge period, the meals comprise lactose. In some embodiments, the meals during the challenge period do not comprise gluten or FODMAPs. In some embodiments, the meals during the challenge period comprise varying amounts of lactose.

The meal set for the elimination period of lactose can be for a number of days that is sufficient for allowing lactose to be sufficiently removed from the body. For example, the elimination period can for about 2-14 days; for example, for 2, 3, 4, 5, 6, 7, 8, 9, 10, 11, 12, 13, or 14 days. In some embodiments, the elimination period can be for about 2-10 days. For some embodiments, the elimination period can be for about 2-7 days. For some embodiments, the elimination period can be for about 2-5 days.

The meal set for the challenge period of lactose can be for a number of days that is sufficient for allowing the body to react to lactose. For example, the challenge period can for about 1-21 days; for example, for 1, 2, 3, 4, 5, 6, 7, 8, 9, 10, 11, 12, 13, 14, 15, 16, 17, 18, 29, 20, or 21 days. For some embodiments, the challenge period can be for about 7-14 days. For some embodiments, the challenge period can be for about 7, 10, or 14 days. In some embodiments, the challenge period can be about 1-7 days, 1-6 days, 1-5 days, 1-4 days, 1-3 days, or 1-2 days. In some embodiments, the challenge period can be about 2-7 days, 2-6 days, 2-5 days, 2-4 days, or 2-3 days. In certain embodiments, the challenge period can be 1 day. In certain embodiments, the challenge period can be 2 days. In certain embodiments, the challenge period can be 3 days.

In various embodiments, a kit for determining the likelihood of having a FODMAP intolerance or sensitivity. Thus, the standardized meal set is configured for that determination. During the elimination period the meals do not comprise FODMAPs (fermentable oligosaccharides, disaccharides, monosaccharaides, and polyols). In some embodiments, the meals in the elimination period also do not contain gluten and/or lactose. During the challenge period, the meals comprise FODMAPs. In some embodiments, the meals in the challenge period do not contain gluten and/or lactose. In some embodiments, the meals during the challenge period comprise varying amounts of FODMAPs.

The meal set for the elimination period of FODMAPs can be for a number of days that is sufficient for allowing FODMAPs to be sufficiently removed from the body. For example, the elimination period can for about 2-14 days; for example, for 2, 3, 4, 5, 6, 7, 8, 9, 10, 11, 12, 13, or 14 days. In some embodiments, the elimination period can be for about 2-10 days. For some embodiments, the elimination period can be for about 1-7 days. For some embodiments, the elimination period can be for about 2-7 days. For some embodiments, the elimination period can be for about 2-5 days. In certain embodiments, the elimination period can be for about 7 days.

The meal set for the challenge period of FODMAPs can be for a number of days that is sufficient for allowing the body to react to FODMAPs. For example, the challenge period can for about 2-21 days; for example, for 2, 3, 4, 5, 6, 7, 8, 9, 10, 11, 12, 13, 14, 15, 16, 17, 18, 29, 20, or 21 days. In some embodiments, the challenge period can be for about 5-21 days. For some embodiments, the challenge period can be for about 7-14 days. For some embodiments, the challenge period can be about 1-7 days. For some embodiments, the challenge period can be for about 7, 10, or 14 days.

In various embodiments, a kit for determining the likelihood of having a fat sensitivity. Thus, the standardized meal set is configured for that determination. During the elimination period the meals do not comprise fats, comprise low amounts of fats, do not comprise certain types of fats (e.g., the type of fat that is believed to be responsible for the sensitivity) or only comprise certain types of fats (e.g., the types of fats that are not believed to be responsible for the sensitivity). In some embodiments, the meals in the elimination period also do not contain gluten, lactose and/or FODMAPs. During the challenge period, the meals comprise fats, high amounts of fats, or certain amounts of the types of fats that were not present in the elimination period. In some embodiments, the meals in the challenge period do not contain gluten, lactose and/or FODMAPs.

The meal set for the elimination period of fats can be for a number of days that is sufficient for allowing the fats to be sufficiently removed from the body. For example, the elimination period can for about 2-14 days; for example, for 2, 3, 4, 5, 6, 7, 8, 9, 10, 11, 12, 13, or 14 days. In some embodiments, the elimination period can be for about 2-10 days. For some embodiments, the elimination period can be for about 1-7 days or 7-14 days.

The meal set for the challenge period of fats can be for a number of days that is sufficient for allowing the body to react to the fats. For example, the challenge period can for about 1-14 days; for example, for 2, 3, 4, 5, 6, 7, 8, 9, 10, 11, 12, 13, 14 days. In some embodiments, the challenge period can be for about 1-7, or 7-14 days.

In various embodiments, a kit for determining the likelihood of having a protein sensitivity or intolerance. Thus, the standardized meal set is configured for that determination. During the elimination period the meals do not comprise certain proteins (e.g., the protein believed to be the cause of the intolerance or sensitivity). In some embodiments, the meals in the elimination period also do not contain gluten, lactose and/or FODMAPs. During the challenge period, the meals comprise the protein or proteins that were not present in the elimination period. In some embodiments, the meals in the challenge period do not contain gluten, lactose and/or FODMAPs.

The meal set for the elimination period of protein(s) can be for a number of days that is sufficient for allowing the protein(s) to be sufficiently removed from the body. For example, the elimination period can for about 2-14 days; for example, for 2, 3, 4, 5, 6, 7, 8, 9, 10, 11, 12, 13, or 14 days. In some embodiments, the elimination period can be for about 2-10 days. For some embodiments, the elimination period can be for about 1-7 days or 7-14 days.

The meal set for the challenge period of protein(s) can be for a number of days that is sufficient for allowing the body to react to the protein(s). For example, the challenge period can for about 1-14 days; for example, for 2, 3, 4, 5, 6, 7, 8, 9, 10, 11, 12, 13, 14 days. In some embodiments, the challenge period can be for about 1-7, or 7-14 days.

In various embodiments, a kit for determining the likelihood of having a chemical sensitivity or intolerance. Thus, the standardized meal set is configured for that determination. During the elimination period the meals do not comprise certain chemicals (e.g., the chemicals believed to be the cause of the intolerance or sensitivity). In some embodiments, the meals in the elimination period also do not contain gluten, lactose and/or FODMAPs. During the challenge period, the meals comprise the chemical(s) that were not present in the elimination period. In some embodiments, the meals in the challenge period do not contain gluten, lactose and/or FODMAPs.

The meal set for the elimination period of chemicals can be for a number of days that is sufficient for allowing the chemical to be sufficiently removed from the body. For example, the elimination period can for about 2-14 days; for example, for 2, 3, 4, 5, 6, 7, 8, 9, 10, 11, 12, 13, or 14 days. In some embodiments, the elimination period can be for about 2-10 days. For some embodiments, the elimination period can be for about 1-7 days or 7-14 days.

The meal set for the challenge period of chemical(s) can be for a number of days that is sufficient for allowing the body to react to the chemical(s). For example, the challenge period can for about 1-14 days; for example, for 2, 3, 4, 5, 6, 7, 8, 9, 10, 11, 12, 13, 14 days. In some embodiments, the challenge period can be for about 1-7, or 7-14 days.

Methods

Various embodiments of the present invention provide for a method of identifying the likelihood of having a food sensitivity or a food intolerance in a subject, comprising: querying the subject regarding one or more symptoms to obtain a baseline score; providing a standardized meal set comprising an elimination meal set and optionally providing a challenge meal set for a testing period; querying the subject regarding one or more symptoms at predetermined time points; collecting the responses relating to the queries; calculating a food and symptom tracker (FAST) score to identify the likelihood of having the food sensitivity or food intolerance. In an embodiment, a FAST instrument (for example, questionnaire) is used to query the subject. In an exemplary embodiment, the FAST instrument is shown in Table 1. In an embodiment, the FAST score is calculated as described herein. In an embodiment, the baseline score is based on a subject's normal (free range) diet.

In further embodiments, the method further comprises providing instructions regarding the timing of the meals.

In various embodiments, the method comprises instructions that the meals for the elimination period are consumed by the subject before the meals for the optional challenge period.

In other embodiments, the method comprises instructions that the meals for the optional challenge period are consumed by the subject before the meals for the elimination period.

In still other embodiments, the subject has no knowledge of whether the meals in the elimination period are consumed first, or whether the meals in the challenge period are consumed first. As such, the subject is "blinded" as to which phase of the test is administered first and which phase of the test is administered second. The instructions are to consume a meal set with a first designation first, and a meal set with second designation second. Examples of first and second designations include but are not limited to A and B, 1 and 2, first and second.

In further embodiments, the method further comprises providing adjunctive instructions. In some embodiments, the adjunctive instructions comprise instructions on liquid ingestions.

In further embodiments, the method further comprises providing tailored guidance about the likelihood of the food sensitivity or food intolerance.

In further embodiments, the method further comprises providing educational material relating to the food sensitivity or food intolerance.

In further embodiments, the method further comprises providing recommended diets to follow based on the subject's input to food preference questions.

In further embodiments, wherein the food sensitivity is FODMAP intolerance, providing recommended diets comprises guidance on how to judiciously re-introduce FODMAPs in a tailored manner.

Standardized Meal Set

The standardized meal set can be as described above and herein.

Food Sensitivity and Intolerance

In some embodiments, the food sensitivity is gluten sensitivity.

In some embodiments, the food intolerance is lactose intolerance.

In some embodiments, the food sensitivity is fermentable oligosaccharides, disaccharides, monosaccharaides, and polyols ("FODMAPs") intolerance or FODMAPs sensitivity.

In some embodiments, the food sensitivity is fat sensitivity, or certain type of fat sensitivity.

In some embodiments, the food sensitivity or intolerance is sensitivity or intolerance to certain proteins.

In some embodiments, the food sensitivity or intolerance is sensitivity or intolerance to certain chemicals.

Testing Period

In various embodiments, prior to testing the subject for food sensitivity or intolerance, a baseline score (for example FAST score) is obtained. In some embodiments, the baseline score is obtained prior to the elimination period. In some embodiments, the baseline score is obtained prior to the elimination and challenge period. In an embodiment, the challenge period is optional.

In various embodiments, the testing period can be for a number of days sufficient to include an elimination period and a challenge period to determine the likelihood of the existence of the food sensitivity. In various embodiments, the testing period can be 4-28 days. In certain embodiments, the testing period can be 6-28, 8-28, 10-28, 14-28, 4-20 days, 6-20, 8-80, 10-20, 4-14 days, 6-14, 8-14, 4-10, 6-10, 8-10 days, 4-8 days. In certain embodiments, the testing period can be 4, 6, 7, 8, 10, 14, 20, 21, or 28 days.

In various embodiments the elimination period can be for a number of days that is sufficient for allowing the body to remove the dietary culprit believed responsible for the food sensitivity or intolerance. In some embodiments, the elimination period can be for a number of days that is sufficient for allowing the symptoms to sufficiently subside after removal of the dietary culprit believed responsible for the food sensitivity or intolerance.

In various embodiments, the elimination period can for about 2-14 days; for example, for 2, 3, 4, 5, 6, 7, 8, 9, 10, 11, 12, 13, or 14 days. In some embodiments, the elimination period can be for about 2-10 days. For some embodiments, the elimination period can be for about 2-7 days. For some embodiments, the elimination period can be for about 2-5 days.

In various embodiments, the challenge period can be for a number of days that is sufficient for allowing the body to react to the dietary culprit. For example, the challenge period can for about 2-21 days; for example, for 2, 3, 4, 5, 6, 7, 8, 9, 10, 11, 12, 13, 14, 15, 16, 17, 18, 29, 20, or 21 days. In some embodiments, the challenge period can be for about 5-21 days. For some embodiments, the challenge period can be for about 7-14 days. For some embodiments, the challenge period can be for about 7, 10, or 14 days.

In various embodiments, the meals for the elimination period are consumed by the subject before the meals for the challenge period. In other embodiments, the meals for the challenge period are consumed by the subject before the meals for the elimination period. In still other embodiments, the subject has no knowledge of whether the meals in the elimination period are consumed first, or whether the meals in the challenge period are consumed first. As such, the subject is "blinded" as to which phase of the test is administered first and which phase of the test is administered second.

The testing period can also be as discussed above with respect to the standardized meal sets.

Symptoms

In various embodiments, the symptoms comprise gastrointestinal symptoms. Examples of gastrointestinal symptoms include but are not limited to abdominal pain, bloating, distension, nausea, vomiting, heartburn, dyspepsia, diarrhea, itching, throat swelling, rashes, lightheadedness, sweatiness, dizziness or shakiness and combinations thereof.

In various embodiments, the symptoms comprise extraintestinal symptoms. Examples of extraintestinal symptoms include but are not limited to fatigue, flushing, sweating, or headache, and combinations thereof.

Symptom Query

In various embodiments, querying the subject regarding the one or more symptoms at predetermined time points comprises a series of timed push notifications on a smartphone, tablet device, or computer that ask the subject regarding the one or more symptoms, at standard intervals following each meal. The queries regarding the symptoms can include queries on ranking the severity of the symptoms, queries on the number of symptoms, queries on the frequency of the symptoms, and/or queries on the duration of the symptoms.

In various embodiments, the predetermined time points are based on when the subject consumes each meal in the standardized meal set.

In various embodiments, collecting the responses relating to the queries comprises using a mobile health application capable of running on a smart phone, tablet device, or computer.

In various embodiments, the responses comprise ranking the one or more symptom from no symptom to worst possible symptom.

In certain embodiments, the responses comprise ranking the one or more symptom from 0 (no symptom) to 10 (worse possible symptom). Other measurements can also be used; for example 0-100, or a numberless visual analogue scale.

Timing of administration and recall period: In an embodiment, querying the subject regarding the one or more symptoms comprises administering/providing the FAST Instrument (questionnaire) to the subject and obtaining response to the questionnaire. Accuracy of symptom burden measurement is improved with increased administration of the FAST Instrument, but this demand must be balanced with patient burden associated with completing questionnaires too often. In an exemplary embodiment, the FAST instrument is as shown in Table 1. A subject who completes the questionnaire inconsistently—e.g., several times a day on some days, and only provoked by symptom flare-ups on other days—will be provided inaccurate information about changes in symptom burden. Thus, data collection using this instrument may be conducted at regular time points, around times when users consume food. In some embodiments, data is collected at irregular intervals or at regular intervals. In some embodiments, the data is collected approximately every 2-4 hours, allowing for 4-8 administrations of the FAST Instrument (questionnaires) per day during the initial phase of development and implementation. According to some embodiments, the MNH application will ask users to think back over the period of time since the last assessment, or alternatively consider the period of time since the last meal.

In order to establish a baseline from which changes in symptoms can be assessed, symptoms are measured based on the subject's typical and/or unrestricted food intake (i.e. free range diet). Users will be prompted to complete the FAST Instrument (for example, questionnaire shown in Table 1) one or more times after agreeing to the dietary challenge. The subjects may be asked to complete the instrument/questionnaire immediately, at a random time points before the end of the day, and/or at the end of a day of typical/normal eating. If a user has skipped meals, or is trying another dietary change, the user must resume typical eating for, for example, a 24 hour period before completing the baseline questionnaire. Multiple intraday administrations of the FAST Instrument/questionnaire at baseline will be used to measure a subject's typical symptom experience given regular diet. These scores will be reduced to single values per domain (average or maximum) for subsequent calculations. For some users, answers to GI PROMIS (the Patient Reported Outcome Measurement Information System funded by the National Institute of Health (NIH)) items encountered while using the MyGIHealth App may be transferred to this program to provide a baseline score.

In an exemplary embodiment, a FAST Instrument comprises the questionnaire as shown in Table 1.

TABLE 1

FAST Score Instrument

| ID | Stem | Response Scale |
|---|---|---|
| S0 | Have you experienced any of the following symptoms?<br>Abdominal Pain<br>Belching<br>Bloating, or feeling fullness in your abdomen<br>"Brain Fog," or problems thinking clearly<br>Constipation | None<br>[Selecting YES to any item will prompt follow-up questions] |

TABLE 1-continued

FAST Score Instrument

| ID | Stem | Response Scale |
|---|---|---|
|  | Diarrhea, or Urgency to use the restroom |  |
|  | Fatigue, or loss of energy |  |
|  | Headaches |  |
|  | Heartburn |  |
|  | Hiccups |  |
|  | Nausea |  |
|  | Passing Gas |  |
|  | Reflux, or stomach contents coming up your foodpipe |  |
|  | Vomiting |  |
| G1A | How bad was your belly pain at its worst? | Severity |
| G2A | How bad did your bloating or fullness feel at its worst? | Severity |
| G2B | How often did you pass gas? | Compare |
| G2C | How often did you feel gurgling or rumbling in your belly? | Compare |
| G3A | How bad was your nausea at its worst? | Severity |
| G3B | How often did you vomit? | Count |
| G4A | Did you have a bowel movement? [YES skips to G4C] | Yes/No (REVERSE) |
| G4B | Did you attempt a bowel movement? [NO skips to G6A] | Yes/No |
| G4C | How much did you strain while attempting your bowel movement? | Amount |
| G4D | Did you feel like there was more still inside of you, that you could not pass? | Yes/No |
| G5A | How often did you have diarrhea? | Count |
| G5B | How often did you have to rush to the bathroom, because you needed to have a bowel movement urgently? | Count |
| G5C | How often did you have a bowel accident (incontinence, or unable to make it to the bathroom in time), or have wet gas (soil yourself when you thought you were just passing gas)? | Count |
| G6A | How bad was your heartburn (burning pain behind the breastbone) at its worst? | Severity |
| G6B | How often did you feel stomach acid or contents come up your food pipe (reflux), or come up into your mouth (regurgitation)? | Compare |
| G7A | How much did you burp up gas from inside your abdomen? | Compare |
| G7B | How much did you hiccup? | Compare |
| X1A | How bad were your headaches at their worst? | Severity |
| X2A | How much did you feel tired, exhausted, or drained of energy? | Amount |
| X3A | How much did you experience "brain fog" - a feeling of mental fuzziness, trouble thinking, or concentrating? | Amount |

In some embodiments, the symptoms in the questionnaire are assigned to a domain score which may be used to compute the FAST score. For example, Belly Pain=G1A; Bloating=G2A; Gas/Flatus=G2B+G2C; Nausea/Vomiting=G3A+G3B; Constipation=G4A+G4B+G4C+G4D; Diarrhea/Urgency/Incontinence=G5A+G5B+G5C; Heartburn/Reflux=G6A+G6B; Burping/Hiccups=G7A+G7B; Migraines=X1A; Fatigue=X2A; "Brain Fog"=X3A.

FAST Score

The FAST score evaluates the strength of association between food ingestions and symptom, using area under the time-to-event curve as an underlying metric.

In various embodiments, the FAST score accounts for the frequency, severity, and multiplicity of symptoms occurring at intervals after a culprit dietary ingestion, and compares symptoms experiences in the elimination vs. challenge periods.

In various embodiments, the subject is compared with himself/herself by statistically evaluating the before vs. after FAST scores.

In various embodiments, each subject is compared to other subjects based on normative FAST scores from other subjects exposed to the same standardized meal set.

In various embodiments, the FAST score a percentile score compared against the general population. For example, a score of 90 indicates the user scored in the 90th percentile compared to others exposed to the same test kit, indicating a high likelihood of a true food sensitivity or intolerance, and a score of 50 indicates a median response.

In various embodiments, a FAST score three standard deviations above the mean FAST score is considered highly suspicious for a true food sensitivity or intolerance; a FAST score of two standard deviations above the mean FAST score is considered moderately suspicious for a true food sensitivity or intolerance.

In an embodiment, the FAST score instrument (questionnaire) response scale is from 0-5, as shown in Table 2a.

TABLE 2a

FAST Score Instrument Response Scales (5-point).

| Value | Amount | Compare | Yes/No |
|---|---|---|---|
| 0 | None at all | Not at all | No |
| 2.5 | A little bit | Less than usual |  |
| 5 | A moderate amount | Same as usual |  |
| 7.5 | A great deal | More than usual |  |
| 10 | An extreme amount | Much more than usual | Yes |

In an embodiment, the FAST score instrument (questionnaire) response scale is from 0-10+, as shown in Table 2b.

TABLE 2b

FAST Score Instrument Response Scales (11-point)

| Count | Severity |
|---|---|
| 0 | 0 |
| 1 | 1 |
| 2 | 2 |
| 3 | 3 |
| 4 | 4 |
| 5 | 5 |
| 6 | 6 |
| 7 | 7 |
| 8 | 8 |
| 9 | 9 |
| 10+ | 10 |

In some embodiments, the FAST score is based on the response scale shown in Table 2a. In some embodiments, the FAST score is based on the response scale shown in Table 2b. In some embodiments, the FAST score is based on the response scale shown in Table 2a and Table 2b.

Questions in the questionnaire are answered using different scales, but the raw values assigned to each scale level produce comparable scores across questions. For example, domain G2 (Gas and Bloating) contains questions that assess severity (measured on a validated 0-10 numerical scale) as well as questions that ask users to compare experiences to their own internal norms (with 5 levels of responses). In order for changes in each question to affect the subscale score equally, scores on questions using 5-point scales are multiplied by 2.5 (reflected in Table 2a), and scores on 11-point questions are used as reported. Additionally, yes/no questions are scored as 0 or 10 depending on the answer chosen. To assess symptom burden, scores within each domain are aggregated as detailed herein. In most cases, time between assessments may remain relatively constant; however, time may still be measured and included in calculations. For each symptom domain, two kinds of variables are computed—area under the curve (AUC) and latency, as described herein.

Area under the Curve (AUC): GI symptoms are continuously changing over time, and these changes are captured over time (for example, using simplified calculus). Traditionally, the area under a continuous curve is calculated using integration, given a formula representing the curve itself. A simplified form of calculation has previously been proposed by Riemann (http://mathworld.wolfram.com/RiemannIntegral.html), where rectangles approximating the area under the curve are used to estimate area. Further, the Newton-Cotes formulas (http://mathworld.wolfram.com/Newton-CotesFormulas.html) are often used to calculate area under the curve using trapezoids. Since the data used herein are not continuous, and naturally form trapezoidal shapes with respect to the X-axis, the Trapezoidal rule for calculating area under the curve may be used (the summation of rectangular and triangular sub-areas).

In an exemplary embodiment, method most recently proposed by Pruessner et al. (Two formulas for computation of the area under the curve represent measures of total hormone concentration versus time-dependent change. *Psychoneuroendocrinology*. 2003; 28:916-31) may be used to process biological data (hormone concentration changes over time, specifically). Two important construct may be used: AUCg, or AUC with respect to the x-axis, representing the total area over time, reflecting symptom level; and AUCi, or AUC with respect to a baseline established at the initiation of data collection. In an embodiment, AUCi may be an important statistic because it captures changes following exposure to a stimulus, rather than total symptoms over time. For example, an individual may report a heartburn severity of 4/10 on the last day of the Elimination Phase, and then report a 6/10 at the end of the first day of the Challenge Phase. If one were to calculate AUCg, the area demarcated by 4 and 6 on the y-axis, over 24 hours on the x-axis, would represent total symptom burden over that day. However, it is more relevant that we calculate the change in symptom experience (2 units increase over those 24 hours), or AUCi.

Formula for calculating AUCg (Pruessner et al. *Psychoneuroendocrinology*. 2003; 28:916-31):

$$AUC_G = \frac{(m_2+m_1) \cdot t_1}{2} + \frac{(m_3+m_2) \cdot t_2}{2} + \frac{(m_4+m_3) \cdot t_3}{2} \frac{(m_5+m_4) \cdot t_4}{2} + \frac{(m_6+m_5) \cdot t_5}{2}$$

Formula for calculating AUCi. (Pruessner et al. *Psychoneuroendocrinology*. 2003; 28:916-31)

$$AUC_i = AUC_G - m_1 \cdot \sum_{i=1}^{n-1} t_i$$

For FAST Score calculation, AUCi may be calculated for each symptom domain, and these areas may be summed for the total FAST Score. This structure allow users to see changes in individual symptoms, as opposed to examining changes in an amorphous "symptom burden" construct. Each domain is reduced to a single score per assessment, and these will be used as the "m" value reflected in the figures above.

Each of these values is used to calculate AUCg and AUCi, using baseline or previous administration values as the point of reference. Notably, Bloating and Gas/Flatus may be combined in a future iteration of this scoring system, but are separated at present.

Latency

It is not only important to establish overall symptom burden over time, and changes in that burden with respect to established time points (food consumption events, days, etc.), but it is also important to establish the time delay between food consumption and symptom change. For example, abdominal gas (belching) is a common experience following consumption of carbonated beverages, and it occurs within minutes of consumption; from it may be concluded that belching and soda are related. An individual with, for example, FODMAP intolerance, may experience constipation hours or days following consumption, may associate that symptom with that type of food. For this reason, latency is calculated for each symptom relative to suspect ingredients.

For symptoms that change in value by a minimal clinically important difference (MCID) compared to the previous assessment:

Latency=(Time of Symptom Report Change)−(Time of FODMAP ingestion).

This information may be used to refine our understanding of the associations between symptoms and food (e.g., what is the average latency between consumption of FODMAPs and heartburn), as well as track individuals' food-symptom experiences, which we expect to vary between patients.

Fast Score Constructs

FAST Momentary Symptom Score: A single value is calculated for each domain based on responses to questionnaire items, and the sum of these values represents a momentary FAST Score (FAST.MOM). Or:

$$FAST.MOM=(G1A)+(G2A)+(G2B+G2C)+(G3A+G3B)+(G4A+G4B+G4C+G4D)+(G5A+G5B+G5C)+(G6A+G6B)+(G5A+G6B)+(G5A+GAB)+(X1A)+(X2A)+(X3A)$$

FAST Daily Symptom Burden Score: AUC can be calculated given at least two FAST Instrument administrations, but is best to calculate once a whole day's worth of data have been collected. Thus, daily symptom burden can be calculated as the sum of the following AUC terms spanning 1 day:

$$FAST.DAY=AUCg\text{-bellypain}+AUCg\text{-bloating}+AUCg\text{-gas}+AUCg\text{-nausea}+AUCg\text{-constipation}+AUCg\text{-soilage}+AUCg\text{-reflux}+AUCg\text{-throat}+AUCg\text{-migraine}+AUCg\text{-fatigue}+AUCg\text{-brain\_fog}$$

FAST Change Score: The change in symptom burden from the previous administration of the FAST Instrument is equal to the sum of all AUCi terms for each domain, or $$FAST.SCORE=AUCi\text{-belly pain}+AUCi\text{-bloating}+AUCi\text{-gas}+AUCi\text{-nausea}+AUCi\text{-constipation}+AUCi\text{-soilage}+AUCi\text{-reflux}+AUCi\text{-throat}+AUCi\text{-migraine}+AUCi\text{-fatigue}+AUCi\text{-brain\_fog}$$

Since the primary purpose of the FAST Score is to track changes in symptoms over time, the primary outcome variable will be the FAST Change Score (FAST.SCORE or FAST Score). In exemplary embodiments, the FAST Score may be reported as a negative value, representing a decrease in symptom burden since the last assessment.

FAST Weekly Change Score: The primary use of the FAST score is to track responses to a week-long intervention designed to detect potential food intolerances. Instead of utilizing a baseline (or previous day's scores) and the current day, the Weekly score is calculated over the whole week, including eight sets of data points (baseline+7 days of Instrument responses). To this end, a weekly FAST score can also be calculated as the sum of the following AUC terms:

$$FAST.WEEK=AUCi\text{-belly\_pain week}+AUCi\text{-bloating week}+AUCi\text{-gas\_week}+AUCi\text{-nausea week}+AUCi\text{-constipation\_week}+AUCi\text{-soilage week}+AUCi\text{-reflux week}+AUCi\text{-throat week}+AUCi\text{-migraine\_week}+AUCi\text{-fatigue\_week}+AUCi\text{-brain\_fog\_week}$$

Standardization

Typically, results of administrations of patient health measurement tools such as PROMIS are reported as percentile ranks, reflecting where a patient stands relative to a national average. Further, summary scores within each domain are composed of different numbers of items. Although each item is scaled similarly, the totals vary by domain. Summing these values, or the AUC values, is problematic because they have not been standardized. Assigning equal weight to each domain through standardization may be equally problematic if the chief symptom changes are within certain domains (e.g., bloating), but this inconsistency will occur across users.

Thus, all FAST scores (including momentary values used to calculate AUC) are standardized. In exemplary embodiments, strategies that may be used to approximate standardization include calculating domain values as the proportion of the maximum total score for that domain, times 100. These values may be used for all subsequent AUC calculations. FAST Scores may be reported as a proportion of the maximum possible value for that score. The FAST Score is useful for measuring total symptom burden, and changes in symptom burden over time. The numerical value does not account for food ingestion, specifically, but can be used for tracking changes in symptoms during a structured dietary program.

My Nutrition Health (MNH) Application

The MNH application can be implemented in software, firmware, and or hardware on a variety of computing equipment, including a desktop computer, laptop computer, web-based thin client, tablet, smart phone, or other processing device. For the purposes of the exemplary discussion herein, the MNH application is presented as implemented on a smart phone such as the iPhone, with the understanding that this exemplary implementation is non-limiting and the application may be implemented on other processing devices based on the teachings herein.

According to some embodiments, a method is provided to, via the MNH application detailed herein, administer a customized assessment of gastrointestinal (GI) symptoms and diet and, depending on that assessment, provide a diet intervention including customized education and training, meal plans, shopping lists, and additional supporting materials and information. The MNH application tracks meals and symptoms during the adjusted diet, and provides reports and scoring accordingly, which can be used to determine if the adjusted diet resulted in an improvement for the participant. Depending on the results, additional support, tools, products, and/or dietary modifications may be provided. Additional exemplary methods for using the MNH application to assist with nutritional assessment and intervention are further detailed with regard to FIG. 14, below.

Figure 6:
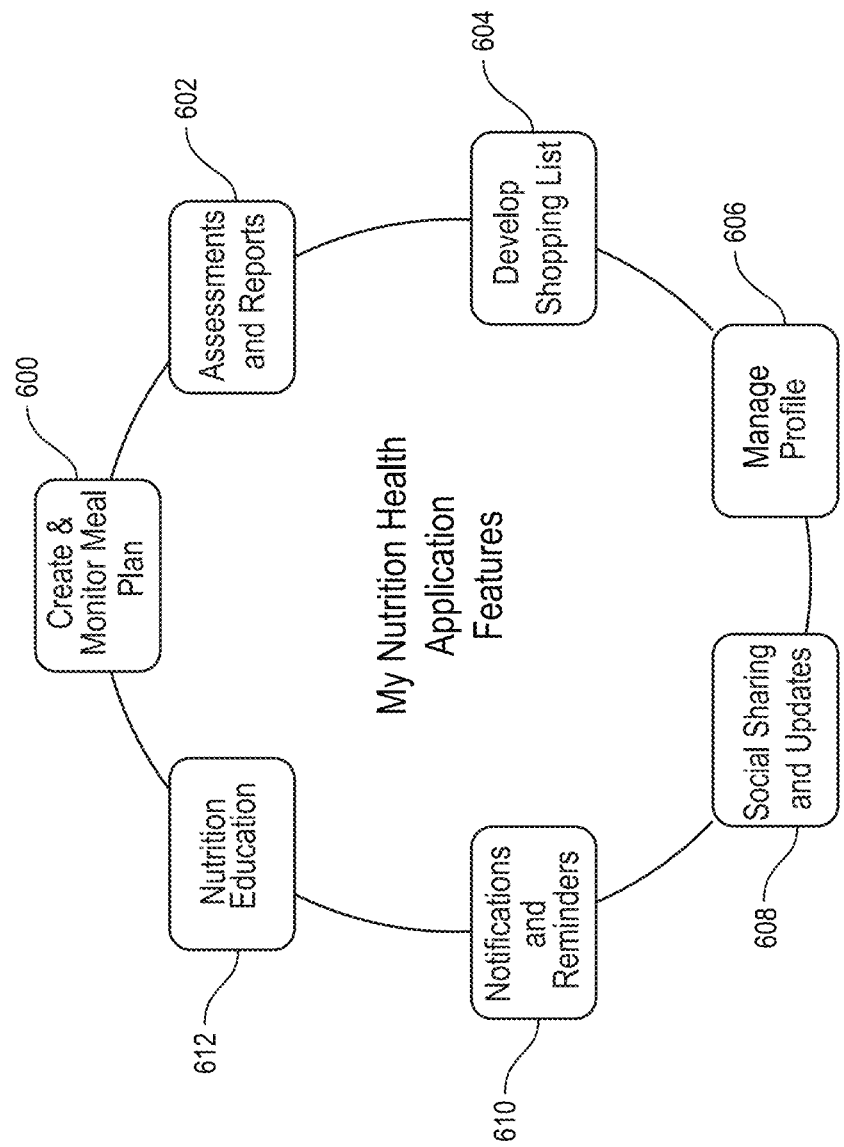
FIG. 6 illustrates exemplary features provided by the my nutrition health (MNH) application, according to an embodiment of the present disclosure.

Turning to FIG. 6, features provided by the MNH application are detailed. The MNH application provides numerous features to systematically test for potential food sensitivities or intolerances, such as gluten sensitivity, lactose intolerance, and FODMAPs sensitivity, as well as other potential nutrition or digestive concerns, and provide detailed assistance with individualized dietary modifications according to the findings.

At 600, the MNH application offers a process to create and monitor a meal plan. According to some embodiments, the meal plan may be customized by the user by selecting from a set of proposed meals corresponding to a recommended diet, such as a low-FODMAP diet or gluten-free diet. Additionally or alternatively, the user may select from a baseline assessment, elimination plan, challenge plan, or combination thereof. A baseline assessment monitors a participant's current diet, and according to some embodiments also compares symptoms when eating in contrast with periods of fasting. An elimination plan provides a modified diet eliminating one or more potential dietary triggers, such as FODMAPs, gluten, lactose, or others. A challenge plan provides a controlled introduction of one or more potential triggers, and may be used in combination with the elimination plan to provide additional information in regard to potential dietary triggers. Importantly, once a meal plan is selected, the MNH application provides monitoring capabilities and reminders to ensure that meals are eaten on schedule and symptom questionnaires are completed at the proper time after each meal. Thus, the MNH application systematically compiles information that may be used for reporting and analysis purposes 602 and other purposes.

At 602, the MNH application provides assessment of symptoms and a variety of scoring and reporting mechanisms. According to some embodiments, the assessment is performed by presenting the participant with a series of questions to identify GI-related symptoms. Additionally or alternatively, an assessment is performed by presenting the participant with one or more questionnaires prior to starting a meal plan to initially assess dietary intake and potential symptoms. Responses to questions are stored and analyzed in order to provide a variety of reports, including a daily report, heatmap report, FAST score report, or similar report relating to potential dietary symptoms.

At 604, the MNH application can provide a specific shopping list of necessary ingredients. According to some embodiments, a shopping list may be selected by the user based on a desired type of diet. According to other embodiments, a shopping list is automatically generated based on the selected meal plan.

At 606, the MNH application provides tools to manage a participant profile. For example, profile management may include user preferences, account information, password change, or other configuration settings.

At 608, the MNH application provides the ability to share updates and other information, such as meal plan progress and reports, via email, text, facebook, twitter, or other social sharing tools.

The MNH application provides notifications and reminders 610, including but not limited to reminders that assist with the meal monitoring and symptom assessment process.

At 612, the MNH application provides specific nutrition education on potential dietary concerns. According to some embodiments, the nutrition education is customized for the participant based on his or her current assessment. Nutrition education features may include frequently asked questions, training modules, animated videos, dietary modification guides, and other features. According to some embodiments, the education features include the capability to present questions to or review common answers from a registered dietician or other nutrition professional.

In addition to the above features, the MNH application may be configured or customized to support additional features such as: branded food items designed to comply with selected diets, targeted offerings based on dietary data, direct sales of pre-packaged meals compliant with dietary restrictions, options to select pre-configured meal plans or shopping lists, directed referrals to providers such as nutritionists or doctors based on symptom data, fee-based consultation with dietician via in-application consultation, subscription based access to enhanced application functions, direct linking or referrals to approved partners for food, prescriptions, information, and other offerings, and other customized offerings. According to some embodiments, the MNH application provides tiered offerings, such as providing basic meal plans and monitoring at a base level, and additional features such as enhanced education offerings, meal plans, reintroduction directions, or other enhancements at a preferred level, which may be based on subscription status, in-app purchases, promotional offerings, or other method of managing enhanced application features.

The MNH application is capable of collecting and aggregating participant data from its participant base, and therefore generating a large volume of valuable clinical information that may be used for research, investigation, and/or commercial purposes. For example, aggregated participant data may be further analyzed to determine the effect of specific foods on the general user population, and therefore develop insights on beneficial or non-beneficial foods. Additionally or alternatively, the aggregated data may be analyzed to identify potential nutritional gaps and/or develop specific foods to address a particular nutritional need. As yet another example, the database of dietary information created by use of the MNH application can be used to develop additional educational programming, dietary recommendations, and other content.

Figure 7:
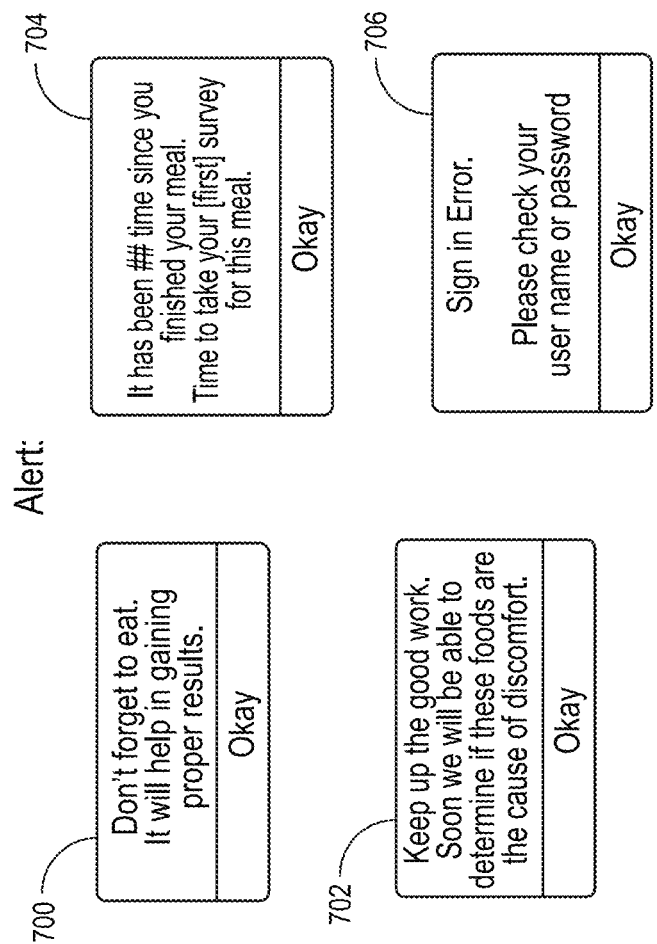
FIG. 7 illustrates exemplary reminders and notifications, according to an embodiment of the present disclosure.

Turning to FIG. 7, exemplary notifications and reminders 610 are illustrated. At 700, a meal reminder is shown. A meal reminder is provided to remind the participant to eat at certain times to achieve the best results from the process. According to some embodiments, when the reminder 700 is presented, the participant may click the reminder to be taken to the current reports display (see, e.g., FIG. 12b) corresponding to the meal plan in progress. At 702, a notification is provided to encourage the participant. In this example, the participant has just begun the first day of a challenge and it is desirable to provide encouragement to build the participant's morale. Once "ok" is selected, the notification closes. At 704, a reminder to complete a survey is provided, to alert the participant that sufficient time has elapsed since a recently completed meal, and it is now appropriate to take a symptom survey for that meal. According to some embodiments, the reminder 704 tells the participant how long it has been since the last meal, and upon clicking the reminder, the participant is taken to the first question of the survey (see, e.g., FIG. 12e). At 706, a notification that the participant has not successfully completed the login process is shown. It is understood that the reminders and notifications 610 discussed herein are exemplary only, and that additional notifications and reminders may be provided as desired for a specific implementation of the MNH application.

Turning to FIG. 8a, a method for sharing information, achievements, reports, and other information from the MNH application is provided. As shown in FIG. 8a, the MNH application is configured to support text messaging 800, email 802, social media such as twitter 804 and Facebook 806, and other communication mechanisms. According to some embodiments, in-application communication mechanisms may be configured through profile management 606. If a communication icon is selected, the corresponding action is launched. For example, if the user desires to provide a facebook status update, the user may select the facebook icon 806 and the MNH application will provide a display to perform the status update, such as the display shown at FIG. 8b. At 808, an exemplary status update confirming a user's completion of a FODMAP challenge is shown. By similar means, a participant may share their MNH application specific data with friends, doctors, dieticians, sponsors, or other recipients, and the participant may be more likely to complete the diet intervention process through these social communication and support mechanisms.

Figure 9B:
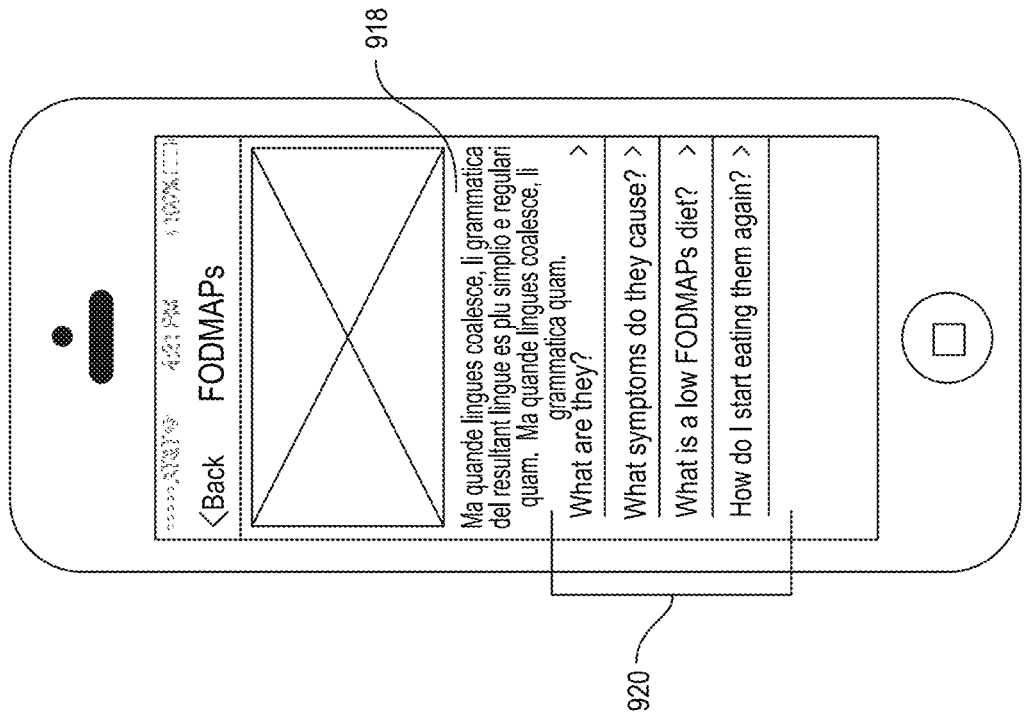
FIGS. 9A (process flow) and 9B-9E (exemplary screen shots) illustrate the nutrition education features, according to an embodiment of the present disclosure.

Turning to FIG. 9a-9e, a process for selecting and presenting education materials is provided. In FIG. 9a, the process begins when a user requests education materials by selecting the education feature in the application, here shown as "My Education" 900. At 902, a display of available education topics is provided. For example, as shown in FIG. 9b, education topics 910, 912, 914 relating to FODMAP, Gluten, and Lactose are displayed for potential selection. A user may then select from the displayed topics, and at 904 the education topic selection from the user is received by the application.

According to some embodiments, educational topics most relevant to the participant are presented for selection, based on the assessment and/or scoring data relating to that user. For example, if the participant was found to be a candidate for FODMAP restriction because an assessment showed that they were eating a significant volume of foods with lactose like dairy products or prepared foods, fructose like soda or various fruits, fructans like wheat, onions or garlic, or polyols like sorbitol, specific education materials on the topic of FODMAPs 910 would be presented to the participant for review.

Figure 9C:
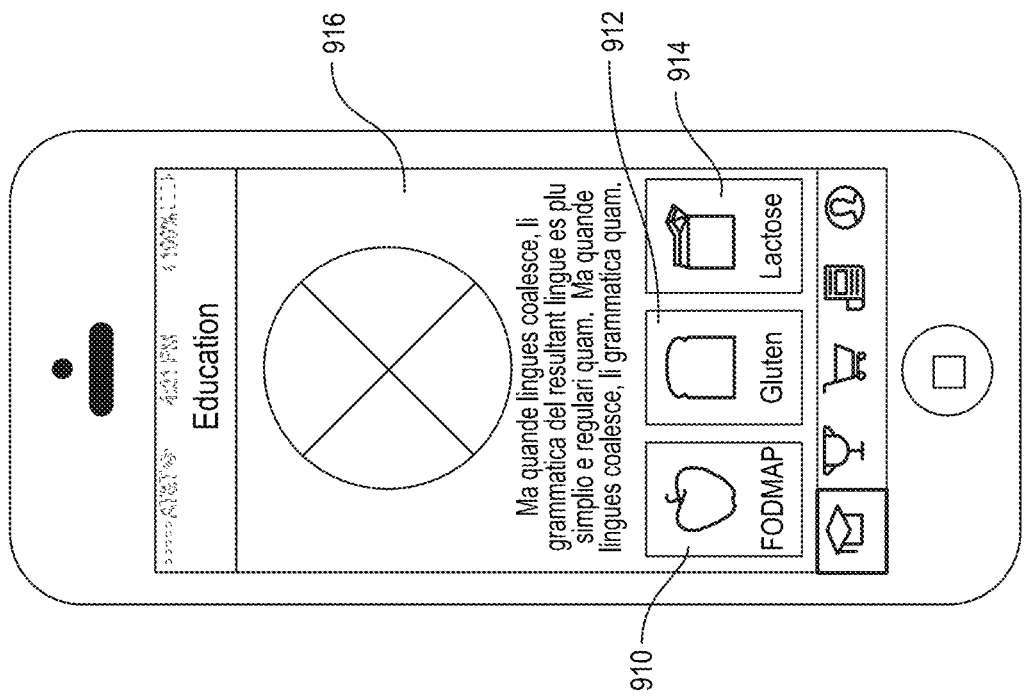

At 906, the application retrieves data relating to the selected topic, and determines if any submenus are available for the listed topic. If no submenus are provided for the selected topic, the process proceeds to 908 and the detailed tutorial begins. But, if submenus are available for the selected topic, then the application displays the appropriate submenus for review and selection by the user. For example, FIG. 9c shows an exemplary display for submenus 920 relating to the FODMAP education topic. Submenu content may include what FODMAPs are, what symptoms they cause, how to eliminate them, and how to reintroduce them so that a participant may find their own diet that hopefully is less restrictive than the full low-FODMAP diet. Thus submenus 920 allow a user to quickly review and jump to a specific section of the tutorial if desired. Upon receiving a submenu selection from the user, at 908, the application will display the corresponding section of the tutorial. According to some embodiments, topic submenus may be further divided into chapters. As an example, the "what are FODMAPs" submenu 920 may include the chapters: introduction, what are FODMAPs really?, what do FODMAPs do?, the 5 FODMAPs, and the FODMAP bucket, and/or other chapters relevant to the submenu 920. Also, at 918, image(s) and text relating to the selected topic are provided. Therefore, through the use of the detailed tutorial 908, comprehensive education materials are provided which allow the user to understand a specific nutritional topic (in this example, FODMAPs) so that the user may know what the dietary item is, how it may affect GI symptoms, how to eliminate and reintroduce it, and related information.

The detailed tutorial 908 may take many forms, including a menu based tutorial, frequently asked questions (FAQs), short videos, animated illustrations, elimination diet guides, and other educational materials.

Figure 9E:
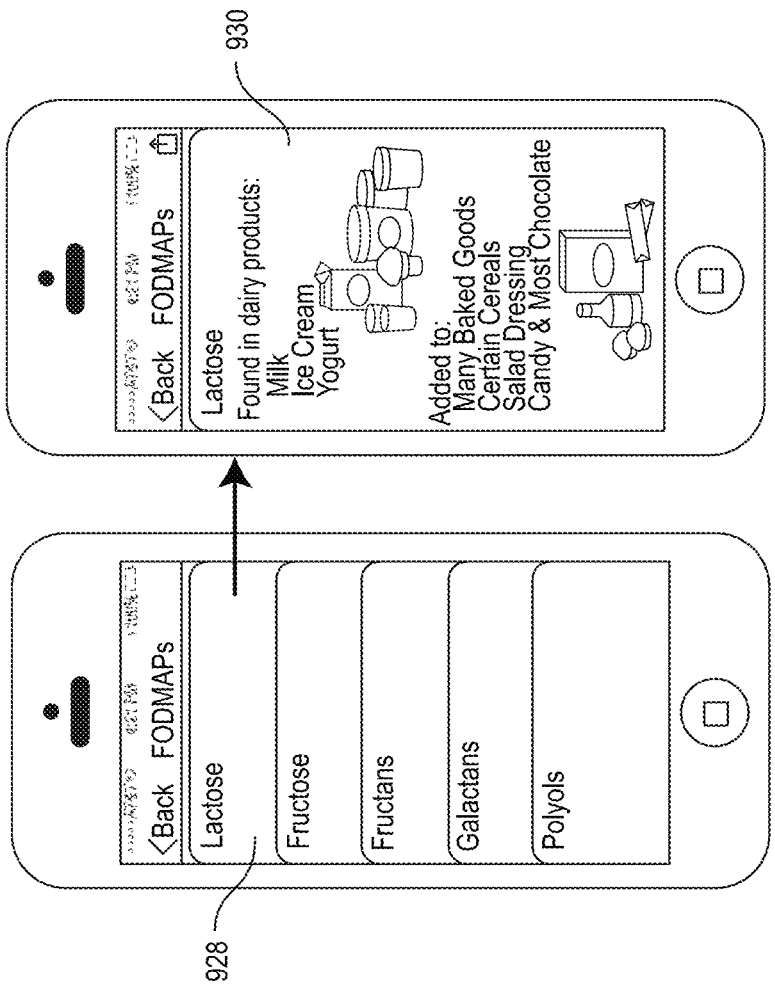
Figure 9D:
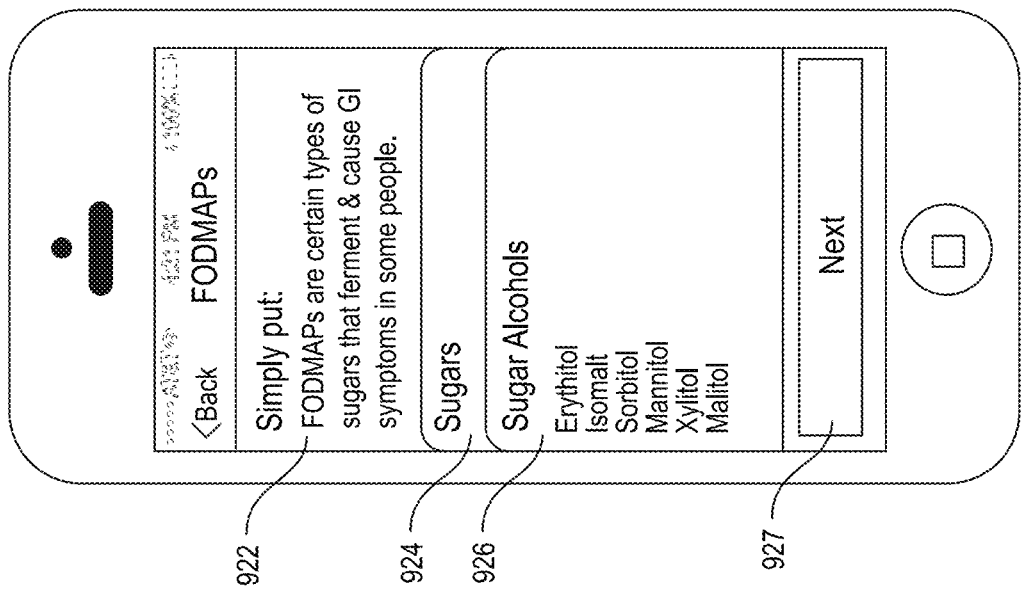

FIGS. 9d and 9e illustrate exemplary displays for a tutorial on the FODMAP topic. The application can display a variety of text, diagrams, pictures, lists, menus, and other content to provide education content on the selected topic. At 922, the exemplary display provides additional data on FODMAPs and allows the user to browse content 924, 926 relating to types of sugars.

Browsing may occur by selecting from content on the display, for example by touching the "lactose" field 928 the display expands to show detailed information regarding lactose 930, as shown in FIG. 9e. Browsing may also occur by selecting "next" 927 or similar icon to proceed to the next page. Other standard mechanisms for browsing content on a computing device, such as forward and back buttons, context sensitive icons, and other mechanisms may be utilized to allow the user to navigate the detailed tutorial 908. According to some embodiments, when a user completes a designated portion of a tutorial, they are provided visual and/or textual feedback to acknowledge the completion and/or provide encouragement.

Turning next to FIGS. 10a-10k, the meal planning feature is detailed through a flowchart (FIG. 10a) and exemplary screen captures of a mobile device running the application (FIGS. 10b-10k), according to an embodiment of the present disclosure. In this example, the meal planning feature is presented as a "challenge," although other types of meal planning (such as but not limited to baseline testing, elimination diet, reintroduction, or combinations thereof) may be included herein, or implemented in alternative embodiments of the application. According to some embodiments, standardized meal kits corresponding with a selected diet may be provided. According to still other embodiments, nutrition bars which are specifically designed to have or not have ingredients relating to a specific food sensitivity or intolerance may be provided. Nutrition bars and/or meal kits are designed to allow medically responsible elimination, and potentially reintroduction, of specific dietary items such as FODMAPs, gluten, lactose, etc. Additionally or alternatively, the participant may only select a type of dietary intervention, and the meals are assigned by the application such that the participant is not aware of the testing phase (e.g. baseline vs. elimination, elimination vs. challenge, etc.) and therefore "blinded" to account for variances in symptom tracking, such as a placebo effect.

Figure 10A:
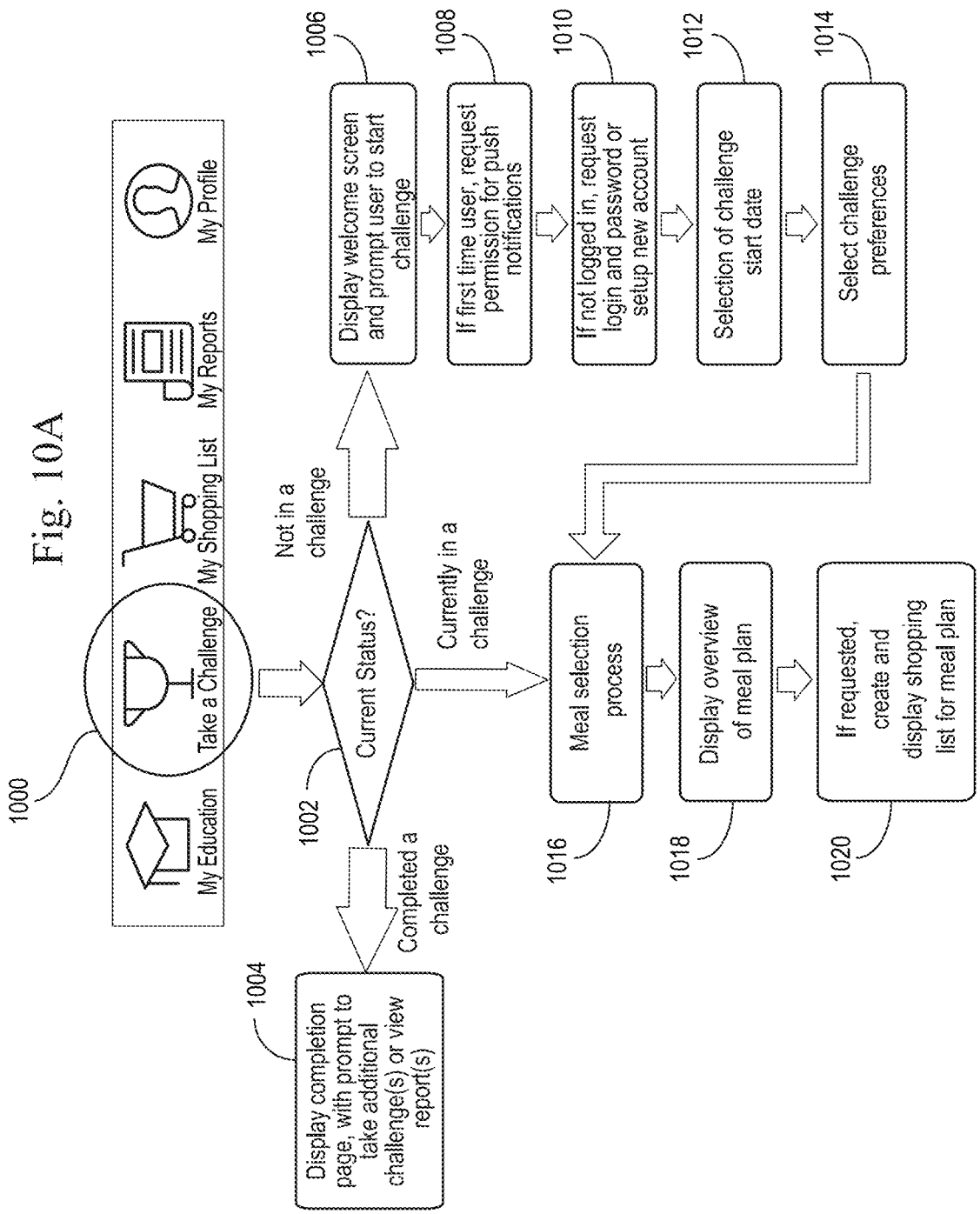
FIGS. 10A (process flow) and 10B-10K (exemplary screen shots) illustrate the meal planning features, according to an embodiment of the present disclosure.

In FIG. 10a, the process begins when a user selects the meal planning feature in the application, shown here as "Take a Challenge" 1000. At 1002, the current challenge status is checked and the appropriate process is then performed by the application based on the current challenge data for the participant. Per the illustrated embodiment, a user may have already completed a challenge, or may be currently participating in a challenge, or is not yet in a challenge. Each option is discussed in turn below.

Figures 10B, 10C:
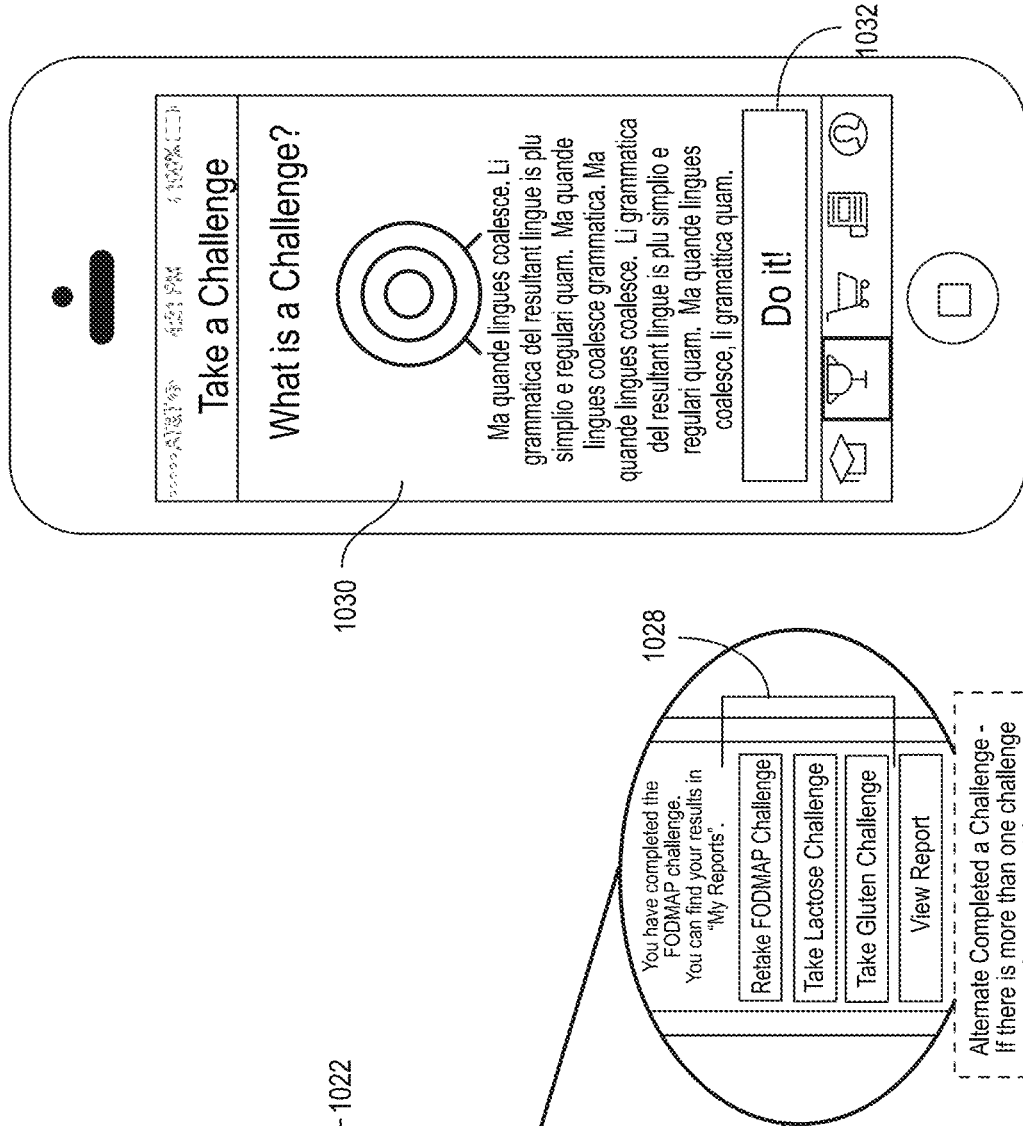

If the participant has completed a challenge, but is not currently in a challenge, the process proceeds to 1004. The application displays a completion page, such as shown in FIG. 10b, which congratulates 1022 the participant on their accomplishment and provides icons 1024, 1026 for additional actions. Additional actions may include viewing one or more reports for each challenge that the user has completed 1026, retaking a previously completed challenge 1024, or beginning new challenge(s). As shown in FIG. 10b, the application is context sensitive and will only display additional actions available to the user at the present time, thus if more than one challenge is available to the user then expanded options 1028 are provided. If a report 1026 is selected, the application proceeds to display the requested report as discussed further below (see, e.g., FIG. 12g). If a challenge is selected, the application proceeds to 1006 and the challenge process begins with selection of start date, then preferences 1014, and meal selection 1016, and so on as explained further below.

Figure 10E:
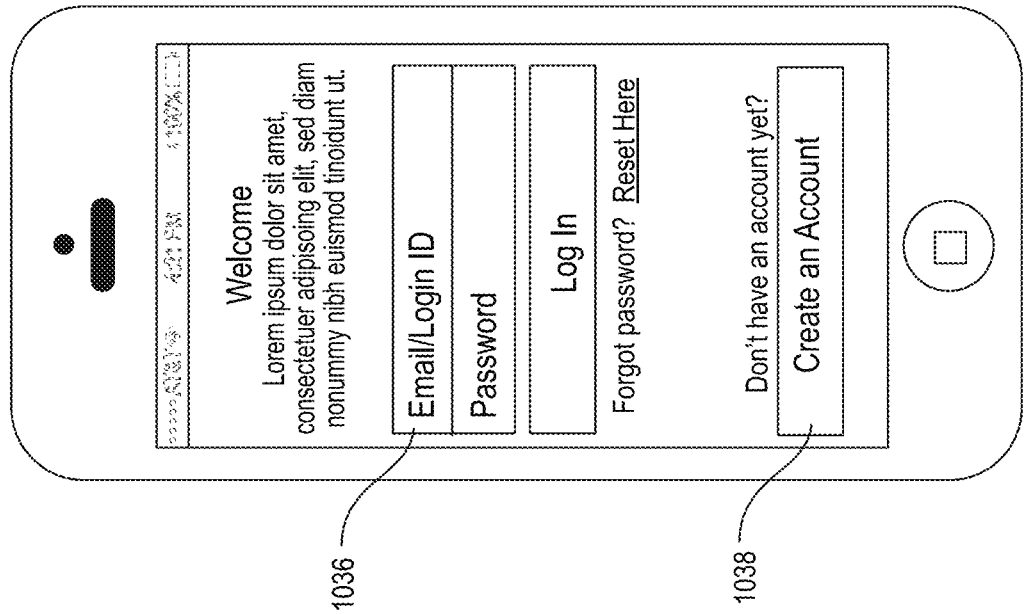
Figure 10D:
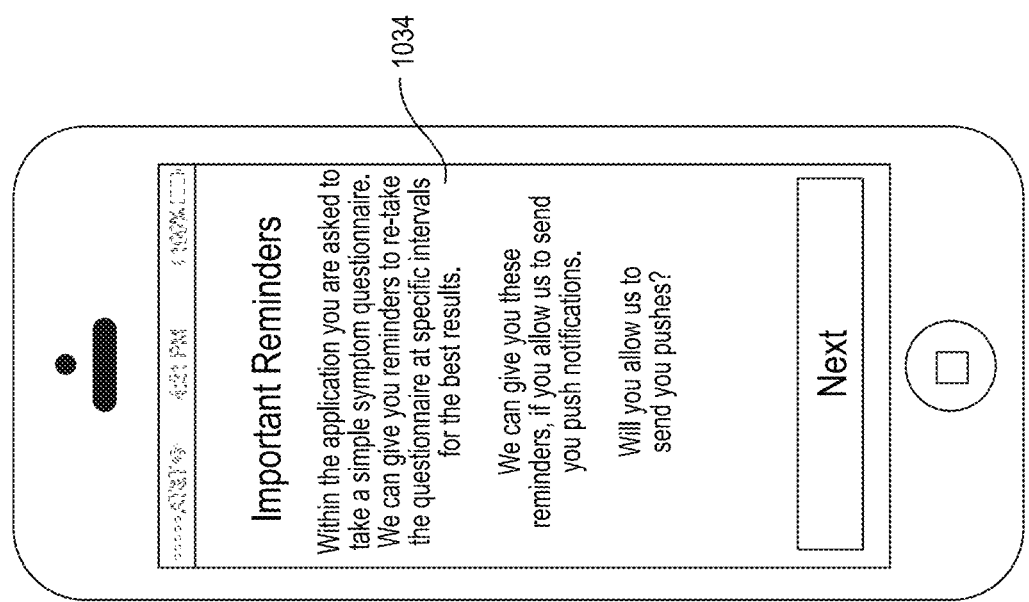
Figure 10I:
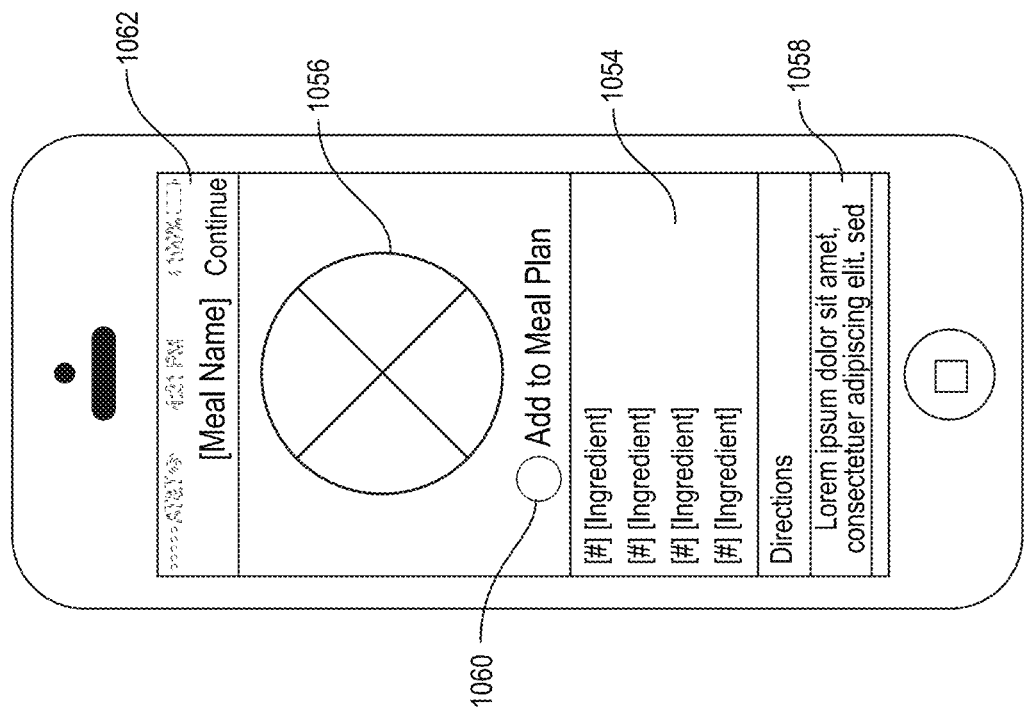

If the user is not in a challenge, then the process proceeds to 1006 and a welcome screen is displayed inviting the user to take a challenge. An exemplary welcome screen is shown in FIG. 10c. The welcome screen may provide pictures and/or text 1030 providing general information, and a selectable icon 1032 to begin. If the user elects to start a challenge by selecting icon 1032, the process proceeds to 1008 and a check is performed to see if the user is a first time user. If so, the application will provide a display such as FIG. 10d asking the user to accept push notifications, so that reminders and notifications may be provided to the user. The process then proceeds to 1010, where the application checks to see if the user is logged in. If so, the process proceeds directly to 1012. If not, a login display is presented, such as shown in FIG. 10e, where a user may enter login and password information 1036 to login to an existing account, or a new account may be created 1038. According to some embodiments, the account creation process prompts the user for permission to access a contacts database, and then imports information from the contacts database to simplify the account creation process.

Upon completion of the login process (if required), the process then proceeds to 1012 where a start date for the challenge is selected. The application will display a date and time selection screen 1040, such as illustrated in FIG. 10f, to prompt the user to decide when the challenge period will begin. According to some embodiments, the user may also have the ability to configure the length of the challenge, the order of diet phases such as elimination and challenge phases, or other parameters.

Next, the process proceeds to 1014 where dietary preferences for the challenge may be collected from the user. According to some embodiments, the challenge participant may exclude certain ingredients, foods, or meals from the challenge, for example because of known dietary restrictions or food allergies. A preference selection display, such as FIG. 10g, is presented to the participant and choices regarding items to exclude from the challenge are collected. According to some embodiments, potentially undesirable ingredients 1042 are listed next to selection boxes 1044, and a participant may indicate that an ingredient is NOT to be used in the study by selecting the corresponding selection box 1044. After the selection of preferences, the process proceeds to 1016 where meal selection is performed.

Figure 10H:
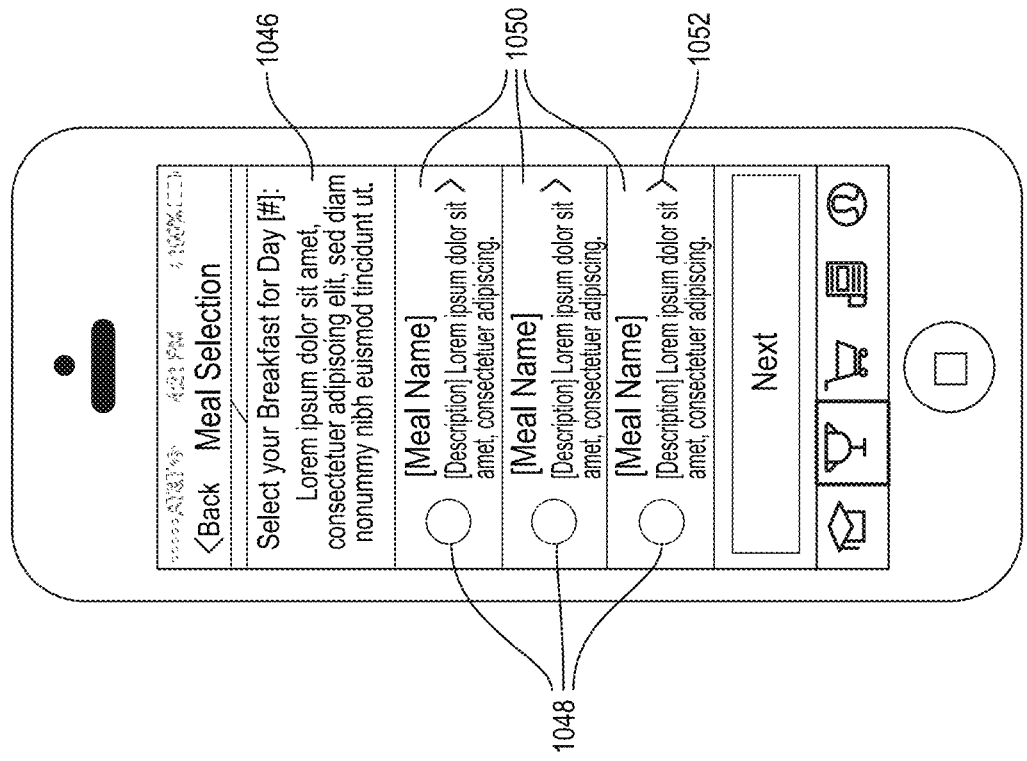

Referring back to 1002, if it is determined that a user is currently in a challenge, the process proceeds directly to meal selection 1016. As shown in FIG. 10h, meal selection allows a user to select each meal successively for each day of the challenge. At 1046, information regarding the meal being selected and the day of the meal plan is provided. According to some embodiments, meals may include breakfast, lunch, dinner, and one or more snacks. A specific meal 1050 may be selected directly from the available options, by selecting the icon 1048 next to the desired meal. Alternatively, the user can get more information about a potential meal via a meal detail display such as FIG. 10*i*, which is presented to the user if the ">" icon 1052 adjacent to the meal in question is selected. The meal detail display provides additional detail about the specific meal selected, such as specific ingredients 1054, an exemplary picture 1056 of the meal, related directions 1058, cooking recipes, and/or other meal-related information. The user may confirm acceptance of this meal from this display, by selecting add to meal plan 1060, and the application will then proceed to meal selection for the next meal. Or, the user may return to the meal selection display, without selecting the current meal, by selecting "continue" 1062.

Once each meal has been chosen for the day, an overview 1064 is presented to the user (see, e.g., FIG. 10*j*). The meal selection process may be continued for the next day, (e.g., by selection of the create day 2 icon 1066), or a shopping list 1068 can be created based on the current meal list—allowing a participant to prepare for the initial portion of the challenge, and select additional meals at a later time. At any point that a shopping list is selected, the process will proceed to create and display a shopping list as discussed further below and as shown in FIG. 11*c*. Until that point, the meal selection process continues as above for each day of the challenge. At the completion of the meal selection process, a complete overview is displayed, such as shown in FIG. 10*k*, allowing a user to review the meals chosen, on a day by day basis, for all challenge meals. Additionally, as a user completes meal selection for each day of the challenge, the option can be presented to display an overview summarizing each completed day.

According to some embodiments, the meal plan may be automatically generated based on one or more initial selections by the user. Additionally or alternatively, the automatically generated meal plan may use standardized meal kits and/or nutrition bars to achieve the desired meal plan. For example, a user desiring a low-FODMAP challenge may select to use standardized meal kits and the application will then populate the elimination and challenge phases with the appropriate meal kits for FODMAP elimination and FODMAP challenge. Thus, the availability of prepared foods, designed for specific dietary assessment and/or intervention, can simplify the meal planning and execution process for the user. According to some embodiments, a user is presented a choice to select between choosing and preparing their own meals or using the prepared meal kits and/or nutrition bars.

Figure 11A:
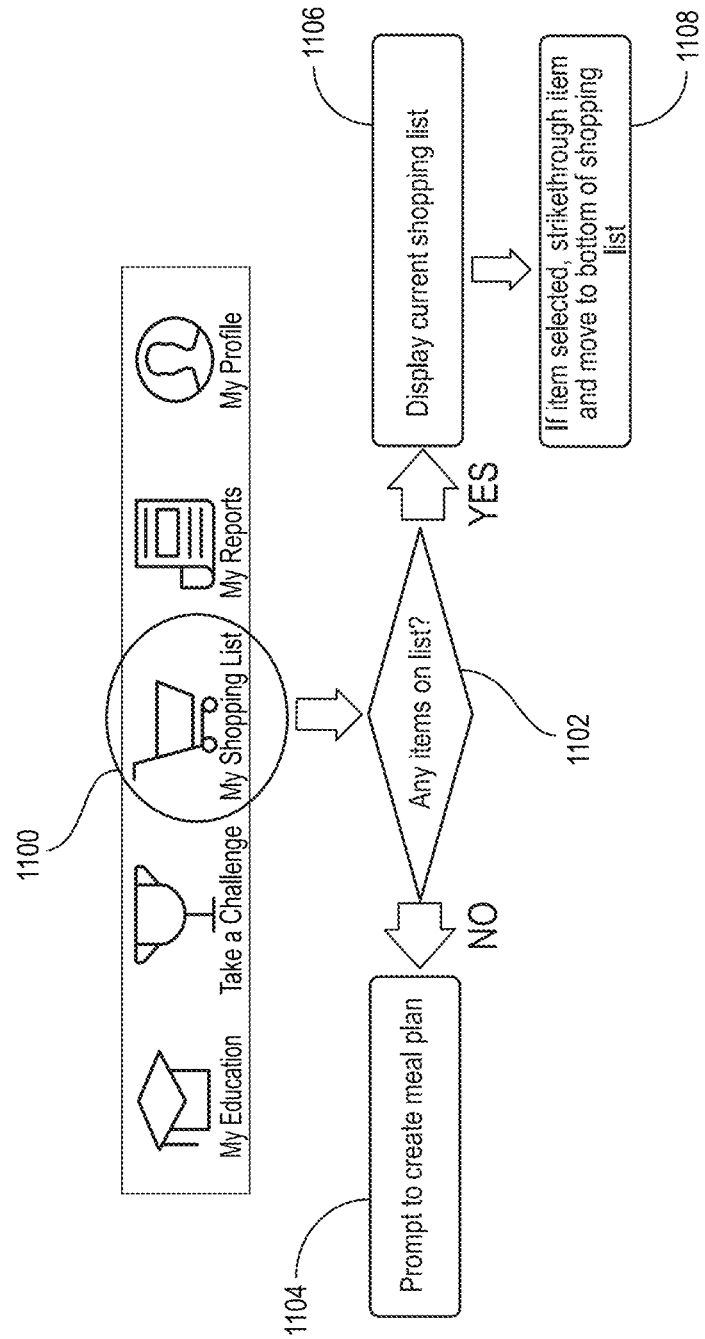
FIGS. 11A (process flow) and 11B-11C (exemplary screen shots) illustrate the shopping cart features, according to an embodiment of the present disclosure.
Figure 11B:
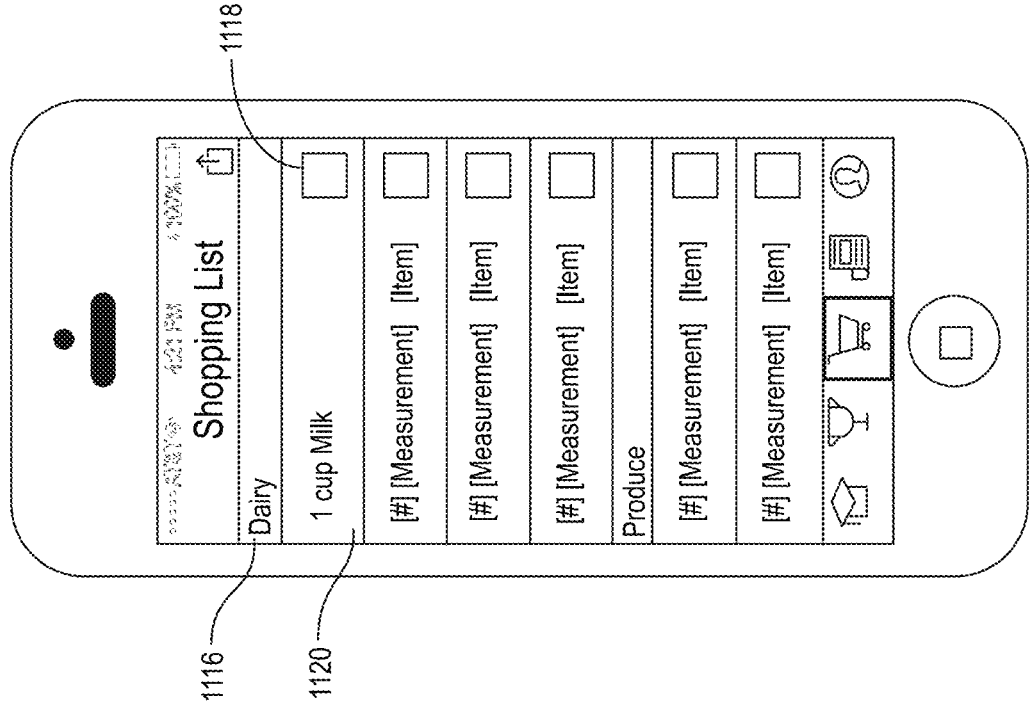
Figure 11C:
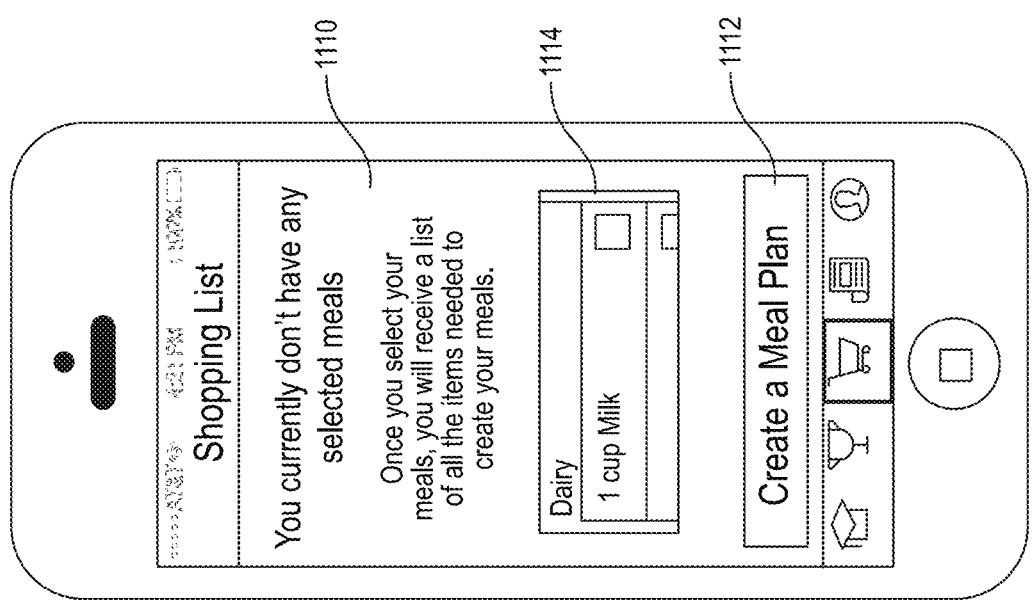

Turning to FIG. 11*a*-11*e*, a process for providing a shopping list for needed ingredients is provided. In FIG. 11*a*, the process begins when a user selects My Shopping List 1100. The MNH application has the capability to prepare a shopping list automatically, based on a selected meal plan. At 1102, a check is performed to determine if any items are on the list. However, if the user has not selected any meals yet, there will not be any items for display on the shopping list, and therefore at 1104 the process will prompt the user to create a meal plan, by presenting a display such as FIG. 11*b*. At 1110, the user is reminded that no meals have been selected. The user may proceed to select create a meal plan 1112, or ingredients can be selected one at a time at 1114.

Returning to 1102, if there are items on the shopping list, the process continues to 1106 where the current shopping list is displayed. An exemplary shopping list is shown in FIG. 11*c*. According to some embodiments, the shopping list is sorted by ingredient type, such that dairy, produce, meat, etc. is grouped together. Additionally or alternatively, sections of the list can be expanded or collapsed by clicking on the desired section. Once an ingredient 1120 is obtained, the check box 1118 can be selected to remove that ingredient from the list. Alternatively, the selection of check box 1118 can be configured to send that ingredient to the bottom of the list. Thus, the MNH application may assist the user during a shopping trip to actively track obtained ingredients, ensuring that all necessary ingredients for the desired meal plan are acquired.

According to some embodiments, the shopping list feature may be combined with targeted offers consistent with a selected meal plan. For example, ingredients on the list may be offered to the user at a discounted rate via the application. Additionally, prepackaged meals complying with the selected diet may be offered directly to the user via the application. Furthermore, other branding and marketing of food items consistent with the specific dietary needs of the participant may be provided by the MNH application.

Figure 12A:
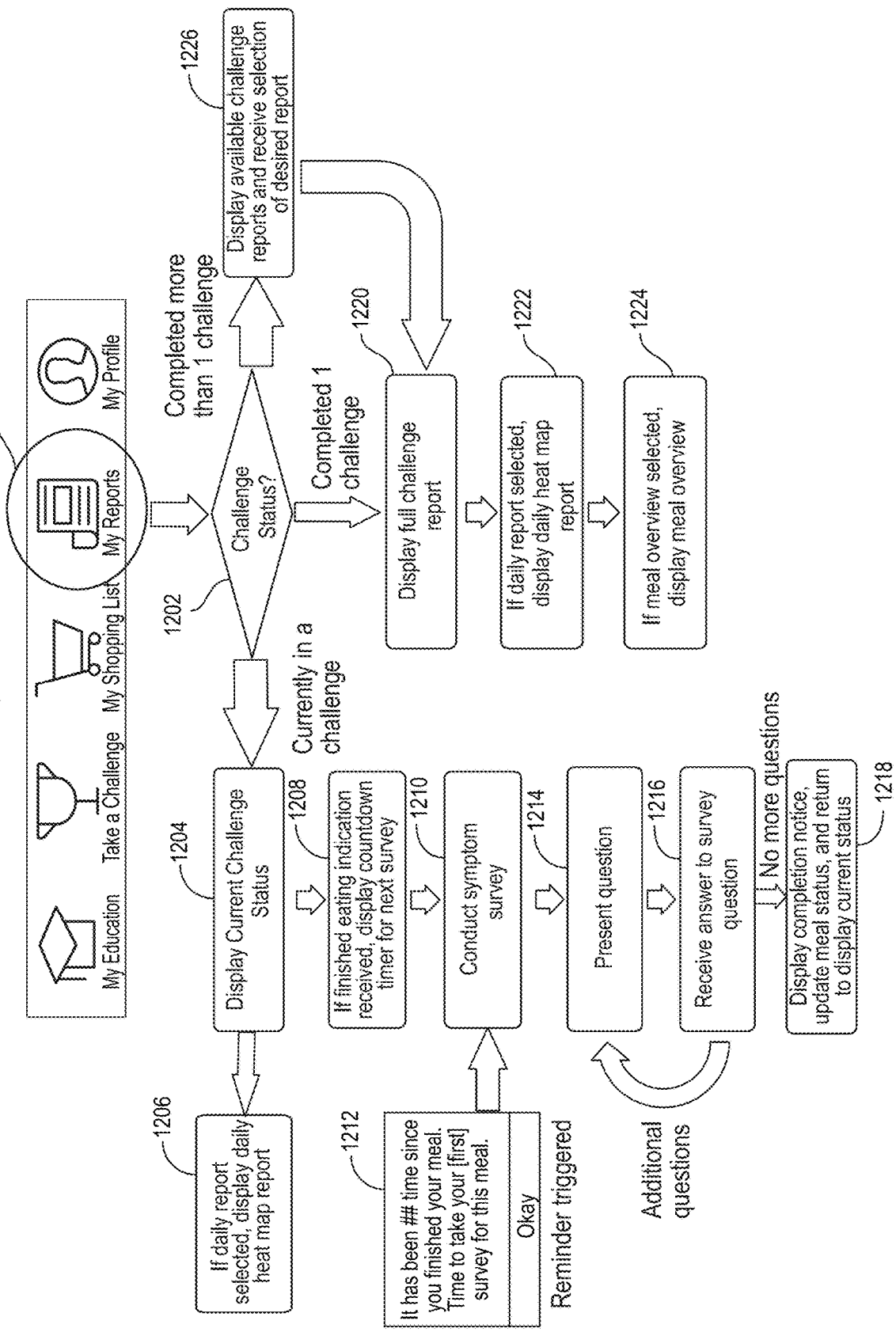
FIGS. 12A (process flow) and 12B-12H (exemplary screen shots) illustrate the assessment and reporting features, according to an embodiment of the present disclosure.
Figure 12C:
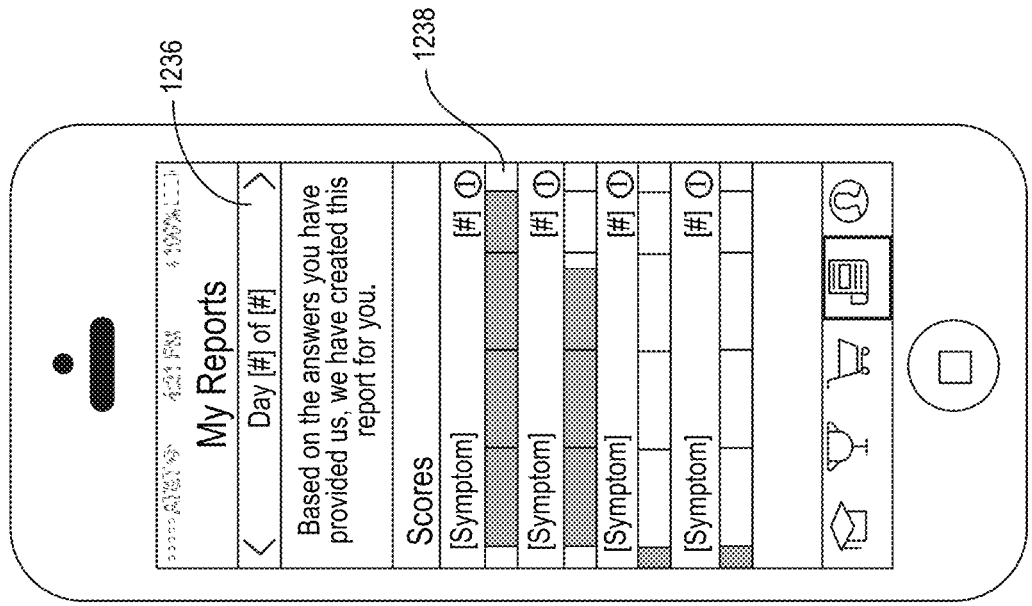
Figure 12B:
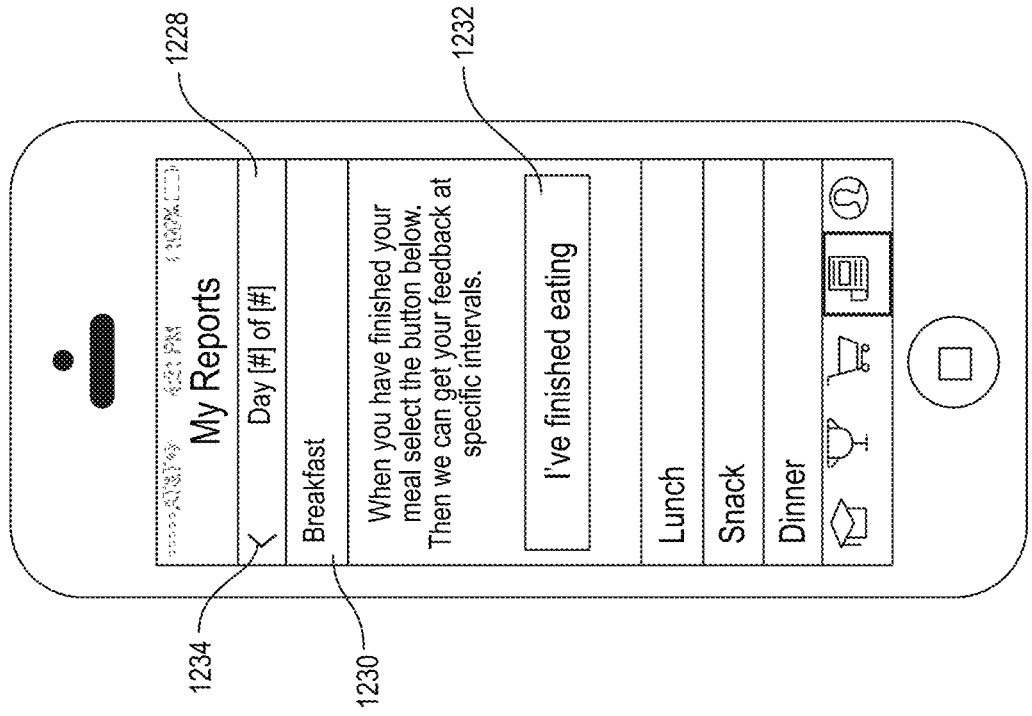

Turning to FIG. 12*a*-12*h*, a process for assessing and reporting symptoms is provided. In FIG. 12*a*, the process begins when a user selects My Reports 1200. The MNH application has the capability to administer a variety of surveys, and provide many reports such as a daily symptom report, FAST score, heatmap report, or summary report to assist in monitoring and evaluating potential dietary issues and symptoms.

At 1202, the current status is checked. If the participant is currently engaged in a challenge, the process continues to 1204 and the current challenge status is displayed (see, e.g. FIG. 12*b*). The current challenge status may include the day 1228 of the challenge, the current meal 1230, and a selection button 1232 to indicate when the current meal is finished. If the left arrow 1234 is selected, the MNH application will proceed to 1206 and display report(s) based on participant information collected so far. The report may provide a textual or graphic representation of particular symptoms, according to meal selection, meal timing, and survey responses. An exemplary report is provided at FIG. 12*c*. At 1236, the applicable period for the report is shown, and may be adjusted (depending on current progress) to show earlier or later time periods of the meal plan. At 1238, a bar graph is used to illustrate the prevalence of particular symptoms. According to some embodiments, the strongest symptom(s) detected are listed at the top of the report. According to other embodiments, the FAST score is reported instead of, or in combination with, the symptom report 1238.

Returning to the current status 1204, if the user selects "I'm finished eating" 1232 then the process proceeds to 1208, where a countdown timer to take a symptom survey is then provided on the display. Upon expiration of the waiting period, the user may select a "take survey" or similar button to conduct a symptom survey 1210 corresponding to the recently completed meal. Alternatively, the MNH application can provide a reminder 1212 that a survey is pending and needs to be completed.

Figure 12E:
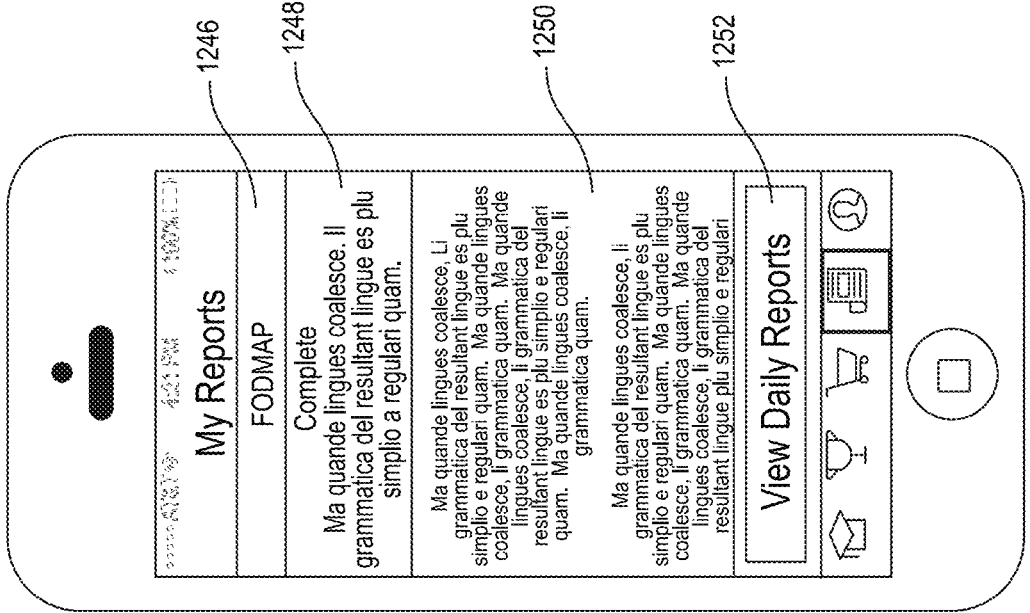
Figure 12D:
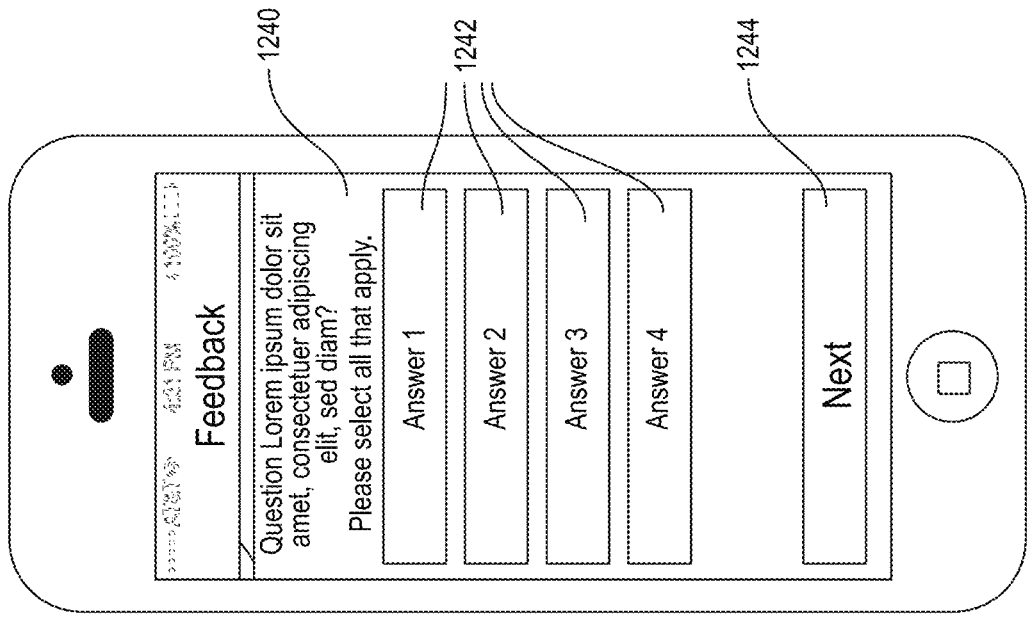

At 1214, the survey process begins by presenting the participant with a question 1240 and a set of potential answers 1242, as illustrated in FIG. 12*d*. Once the most applicable answer is selected, the user may select next 1244 to confirm the selected answer. At 1216, the application receives the answer to the question and determines if additional questions remain. If so, the process returns to 1214 and displays the next question and potential answers to the participant. If no questions remain, the process continues to 1218 and a completion notice is displayed thanking the participant for completing the current survey. The survey completion may also be indicated by a check mark next to the applicable meal 1230 in the status display.

Figure 12G:
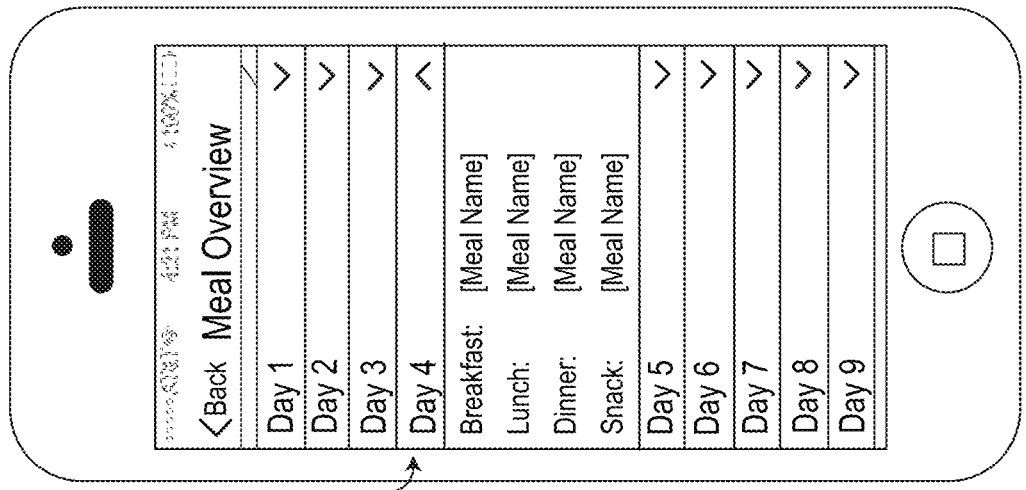
Figure 12F:
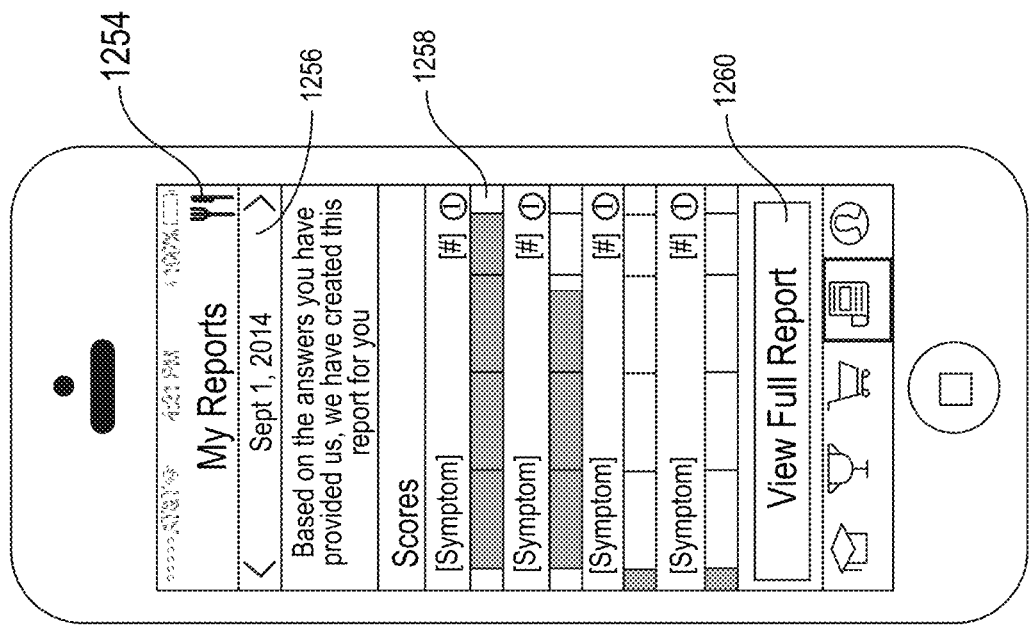

If the current status check at 1202 determines that the user is not currently in a challenge, but one challenge has been completed, then the full challenge report 1220 will be displayed. An exemplary report is shown in FIG. 12*e*, wherein the type of diet 1246, a short status summary 1248, and a detailed report 1250 may be provided to the user. An icon 1252 allows for selection and viewing of daily reports, and if selected, at 1222 a daily report such as in FIG. 12f is provided. The daily report includes a display of the current date 1256 and options to move forward or backward to alternate dates. The report includes visual, textual, and/or numerical scoring 1258 of symptoms. Selection of the full report icon 1260 returns to the display of the full report 1220. If the meal overview button 1254 is selected, the process at 1224 provides a meal overview, so that the user may review the completed meals in the study. An exemplary display of the meal overview is shown at FIG. 12g.

Figure 12H:
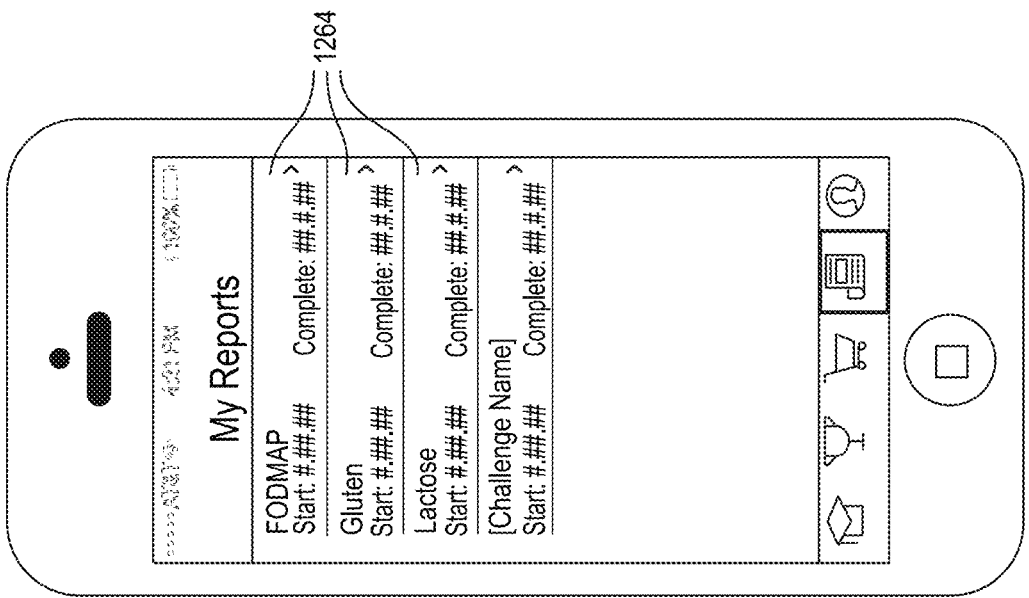

If the current status check at 1202 determines that the user is not currently in a challenge, but more than one challenge has been completed, then the available reports are displayed for selection at 1226. As shown in FIG. 12h, the available reports 1264 are provided for selection by the user, and upon selection of a specific report, that full report is provided at 1220 and the process continues as detailed above.

Figure 13A:
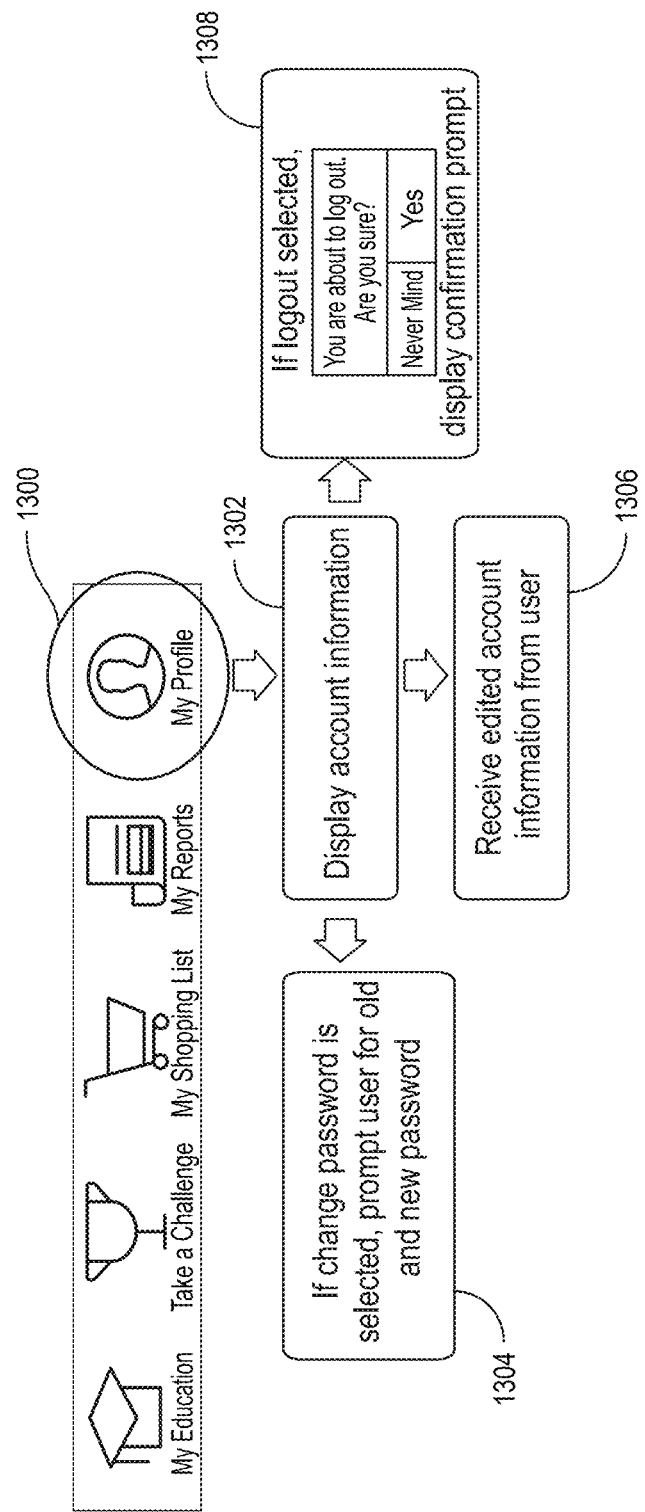
FIGS. 13A (process flow) and 13B (exemplary screen shot) illustrate the profile management features, according to an embodiment of the present disclosure.
Figure 13B:
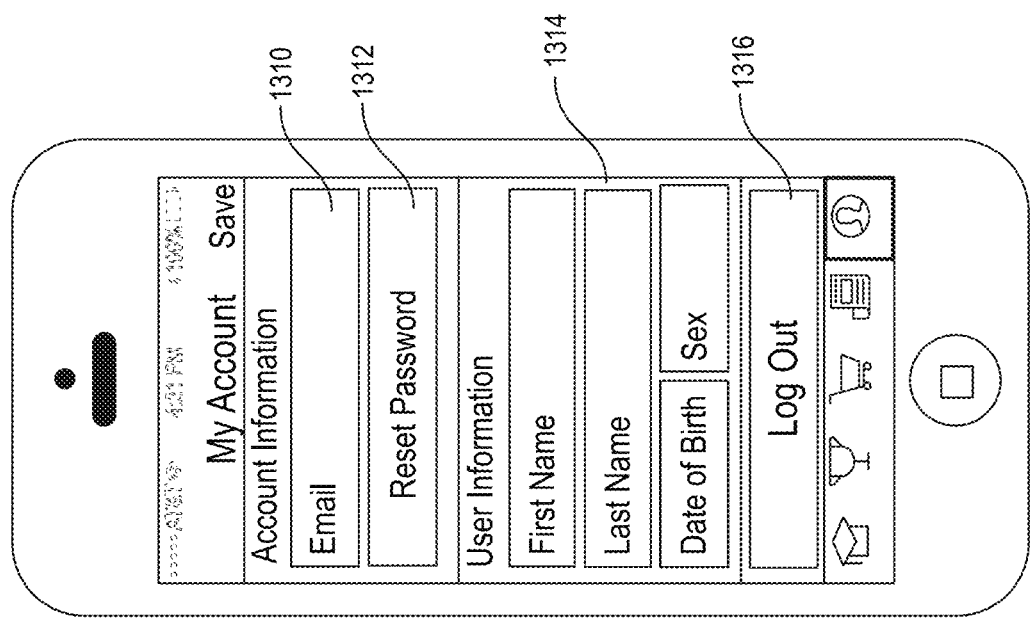

Turning to FIGS. 13a-13b, a process for managing a user's profile is provided. In FIG. 13a, the process begins when a user selects the my profile feature 1300 and the current account information is displayed at 1302. FIG. 13b provides an exemplary display of account information 1302. Based on the desired selection, the process may provide the capability to change the current password at 1304, edit the account or user information at 1306, or logout at 1308. According to some embodiments, additional user configurable parameters may be adjusted using the my profile feature 1300, such as but not limited to default settings, preferred display options, options to receive additional content, and other profile parameters.

According to some embodiments, in addition to the tracking and reporting capabilities discussed above, one or more assessment questionnaires may be provided and analyzed prior to planning and testing a structured diet program. The assessment may follow generally the symptom survey process of 1210-1218, using an initial set of assessment questions such as a food frequency questionnaire (FFQ), GI symptom assessment, FAST score, and/or similar mechanism to provide initial indications relating to a user's current diet. Per this initial assessment, the initial dietary intervention recommendation can be provided earlier in the process. A method for performing early assessment, and tracking dietary interventions, using the MNH application is now detailed in relation to FIG. 14.

At 1400, the MNH application administers a customized assessment of gastrointestinal (GI) symptoms and diet. According to some embodiments, the assessment may evaluate nutrient intake, FODMAP intake, gluten intake, or other dietary factors via a FFQ, and evaluate GI symptoms using the FAST scoring process detailed above. Based on the completed assessment, a determination is made at 1402 as to whether symptoms may be associated with food.

According to some embodiments, if the assessment is performed using the FFQ and FAST scoring process, the determination may be performed as follows. If the participant is not experiencing symptoms, which may be indicated by a "no" response to question S0, or according to other embodiments, a FAST score under a predetermined threshold value, then a dietary intervention is not recommended. Alternatively, if baseline data uncovers significant symptoms, then the FFQ is analyzed to determine whether a trial with a specific dietary intervention would be worthwhile.

If so, the recommended dietary intervention(s) are provided at 1406. For example, an assessment showing a high level of FODMAP intake and related symptoms would inform a low FODMAP dietary intervention. As another example, assessment and symptoms indicating potential gluten intolerance would inform a gluten-free dietary intervention. As yet another example, the assessment may indicate multiple potential dietary issues, and therefore recommend a primary intervention and additional intervention(s) according to the assessment data. Alternatively, if the initial assessment does not indicate symptoms associated with food, at 1404 the user is guided to additional resources for GI assessment and treatment.

Returning to 1406, upon presentation of a recommended dietary intervention the process continues to 1408 where additional resources are provided by the MNH application to teach the user about the recommended intervention. Additional resources may include customized education and training, animated materials on why diet modifications may help, FAQs, elimination guides, meal plans, shopping lists, access to standardized meals, access to coaching from a dietician, and additional supporting materials and information to assist the user with the dietary intervention.

The user may access these resources, and select a meal plan, as discussed above (for example, see generally FIGS. 9a, 10a, 11a and related discussion). Then, as the user performs the modified diet, at 1410 the MNH application is used to track meal compliance and symptoms, and provide reports (for example, see generally FIG. 12a and related discussion). The process at 1410 may use the FAST score and/or other scoring mechanisms to report effects of the modified diet. According to some embodiments, the MNH application may be configured to support image or voice based entry of diet information and/or completion of symptom questionnaires.

At 1412, a determination is made as to whether the participant has an improvement in symptoms per the dietary intervention. According to various embodiments, improvement may be measured by several methods, using the reporting data generated by the MNH application over the course of the dietary intervention. Improvement may be measured by a simple reduction in symptom score, as indicated by a comparison of FAST score, or other measurement data, over time for the dietary intervention. Alternatively, improvement may be determined when the measurement travels below a fixed threshold, for example, the FAST score average for an elimination period of less than 2.5. As yet another method, the AUCi may be evaluated on an absolute or relative basis. On an absolute basis, a negative AUCi value indicates improvement from the initial symptom level. On a relative basis, the AUCi value has to show a statistically significant decrease (for example, a decrease of at least half of one standard deviation relative to the general population) in order to confirm improvement. Other methods of evaluating improvement, using a combination of the scoring methods detailed above, may also be used.

If no improvement is reported, then the process proceeds to 1414, where the application checks for other potential dietary interventions based on the user's information. If another potential intervention is found, it is offered to the user at 1406 and if approved, the education, meal tracking and reporting process continues again from 1408-1410 as discussed above. If no other dietary interventions are appropriate for recommendation, the process goes to 1404 where the user is guided to additional resources for potential GI assessment and treatment.

If improvement is reported at 1412, the process continues to 1416 where, if appropriate based on the report data, the MNH application may instruct the user on the strategic reintroduction of eliminated food(s), allowing the user to tailor their diet in a way that liberalizes their dietary intake and broadens the palate of permitted foods and therefore encourages long term compliance. However, if the report data indicates a strong symptom response to a particular food ingredient, then reintroduction is contraindicated. At 1418, additional actions, resources and monitoring are provided to support the user's personalized diet. Such additional actions and resources may include further recommendation(s) for dietary modifications, continuation of the dietary intervention with additional meals and shopping lists, customized recipes supporting the diet, referral to a dietician for further education and meal planning, offers to receive free samples or purchase of pre-packaged diet-compliant meals, opportunities to connect with a community of MNH application users including potential partners or sponsors to support a revised nutrition lifestyle, and other actions associated with the participant's modified diet. Also at 1418, the user may continue to prepare and track meal plans, and review associated reports, to assist with compliance during the initial diet modification stage.

Thus, the MNH application is able to assess dietary needs, provide one or more dietary interventions and supporting resources, track symptoms during the intervention, report improvement, and assist with additional or continued diet adjustment.

According to aspects of the present disclosure, embodiments may employ one or more network service(s), database (s), and/or application(s) that are executed on a computing device. In some embodiments, the computing device may be a portable device, such as a smart phone or other smart device, such as a computer tablet, watch, etc., and the application may be a mobile application.

To provide aspects of the present disclosure, embodiments may employ any number of programmable processing devices that execute software, or stored instructions. Physical processors and/or machines employed by embodiments of the present disclosure for any processing or evaluation may include one or more networked (Internet, cloud, WAN, LAN, satellite, wired or wireless (RF, cellular, etc.), etc.) or non-networked general purpose computer systems, microprocessors, field programmable gate arrays (FPGAs), digital signal processors (DSPs), micro-controllers, smart devices (e.g., smart phones), computer tablets, handheld computers, and the like, programmed according to the teachings of the exemplary embodiments of the present disclosure, as is appreciated by those skilled in the computer and software arts. In addition, the devices and subsystems of the exemplary embodiments can be implemented by the preparation of application-specific integrated circuits (ASICs) or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present disclosure may include software for controlling the devices and subsystems, for driving the devices and subsystems, for enabling the devices and subsystems to interact with a human participant, and the like. Such software can include, but is not limited to, device drivers, firmware, operating systems, development tools, applications software, database management software, and the like. Such computer readable media further can include the computer program product of an embodiment of the present disclosure for performing all or a portion (if processing is distributed) of the processing performed in implementing the embodiments disclosed herein. Computer code devices can include any suitable interpretable or executable code mechanism, including but not limited to scripts, interpretable programs, dynamic link libraries (DLLs), Java classes and applets, complete executable programs, and the like. Moreover, parts of the processing can be distributed for better performance, reliability, cost, etc.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read. Such storage media can also be employed to store other types of data, e.g., data organized in a database, for access, processing, and communication by the processing devices.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the disclosure. It is also contemplated that additional embodiments according to aspects of the present disclosure may combine any number of features from any of the embodiments described herein.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

A user believes she has symptoms that are related to food. She decides to start with testing for gluten sensitivity. She is provided a standardized meal set and a set of instructions for what to do over a 14-day period. On days 1 through 7, the elimination period, she consumes food that is completely gluten free. She does that by consuming a set of standardized gluten-free meals. The meals include breakfast, lunch, dinner and one snack and contain a standardized volume, total calorie count, and lack of gluten. During the gluten elimination period, she indicates in an app when she consumed each of the test meals and how much of each meal she consumed. The app then takes over and sends push notifications to the user based upon an algorithm. The notifications ask her to report spontaneous symptoms using an ecological momentary assessment (EMA) model. The timing, frequency, amount, and types of symptoms are collected and an individualized profile for that user is created, with an "area under the curve" of symptoms experiences over the gluten-free elimination period. Then, on days 8 through 14, the challenge period, the patient consumes a set of pre-specified test meals that are high in gluten. These have similar volume and calorie count as the elimination period test meals, but are high in gluten. Once again, she will measure her symptoms over the challenge period using the EMA model.

Example 2

A user believes she has symptoms that are related to food. She decides to start with testing for lactose intolerance. She is provided a standardized meal set and a set of instructions for what to do over an 8-day period.

On days 1 through 4, the challenge period, she consumes food that contains lactose. She does that by consuming a set of standardized lactose-enriched meals. The meals are a similar volume, total calorie count, and are enriched-free. During those days, the she indicates in an app when she consumed each of the test meals, and then the app takes over and sends push notifications using an algorithm. The notifications ask her to report spontaneous symptoms using an ecological momentary assessment (EMA) model. The timing, frequency, amount, and types of symptoms are collected and an individualized profile for that user is created, with an "area under the curve" of symptoms experiences over the lactose-enriched test days.

Then, on days 5 through 8, the elimination period, she consumes a set of pre-specified test meals that are lactose-free. These have similar volume and calorie count as the challenge period test meals, but are lactose free. Once again, she will measure her symptoms over the days using the EMA model.

Example 3

A user believes she has symptoms that are related to food. She decides to start with testing for FODMAP sensitivity. She is provided a standardized meal set and a set of instructions for what to do over a 14-day period. She is unaware of whether she is starting the elimination period first or the challenge period first.

On days 1 through 7, the elimination period, she consumes food that is completely free of FODMAPs. She does that by consuming a set of standardized FODMAP-free meals. The meals include breakfast, lunch, dinner and one snack and contain a standardized volume, total calorie count, and are FODMAP-free.

During the FODMAP elimination period, the she indicates in an app when she consumed each of the test meals, and then the app takes over and sends push notifications using an algorithm. The notifications ask her to report spontaneous symptoms using an ecological momentary assessment (EMA) model. The timing, frequency, amount, and types of symptoms are collected and an individualized profile for that user is created, with an "area under the curve" of symptoms experiences over the FODMAP-free test days. Then, on days 8 through 14, the challenge period, she consumes a set of pre-specified test meals that contain FODMAPs. These have similar volume and calorie count as the elimination period test meals, but contain FODMAPs. Once again, she will measure her symptoms over the days using the EMA model.

In some instances, the FODMAP-free meals will also lack gluten and/or lactose to control for those factors.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of performing a dietary assessment and facilitating a dietary intervention for a participant, the method performed by a computing device and comprising:
    assessing the participant's current level of gastrointestinal symptoms and dietary intake of the participant based on the participant's responses collected periodically in response to a series of questions presented by a software application running on the computing device;
    calculating a food and symptom tracker (FAST) score for tracking changes in symptoms over time based on each of the participant's responses to identify the likelihood of the participant having food sensitivity or intolerance;
    recommending a modified diet according to the assessment;
    providing at least one educational resource relating to the recommended modified diet;
    tracking a plurality of meals ingested by the participant consistent with the recommended modified diet; and
    monitoring for symptoms subsequent to each of the plurality of meals.

2. The method of claim 1, further comprising:
    preparing at least one symptom-based report; and,
    determining, according to the at least one symptom-based report, if the participant's symptoms improved as a result of the modified diet.

3. The method of claim 2, further comprising recommending the participant to selectively reintroduce ingredients eliminated in the modified diet.

4. The method of claim 2, further comprising recommending an additional action according to the at least one symptom-based report, wherein the additional action comprises continued tracking of meals and monitoring of symptoms, recommending one or more recipes compliant with the modified diet, or generating a shopping list consistent with the modified diet.

5. The method of claim 1, wherein the assessing of the dietary intake of the participant is performed using a food frequency questionnaire.

6. The method of claim 1, wherein the modified diet comprises a reduced gluten, reduced lactose, reduced fermentable oligosaccharides, disaccharides, monosaccharaides, and polyols ("FODMAPs"), reduced fat, or reduced protein diet.

7. The method of claim 1, wherein the computing device comprises a mobile computing device communicatively coupled to a network.

8. The method of claim 1, further comprising presenting the participant with a plurality of meals consistent with the recommended modified diet, receiving a selection from the participant of one or more meals from the plurality of meals, and generating a shopping list of ingredients according to the selected one or more meals.

9. The method of claim 1, further comprising offering prepackaged meals consistent with the modified diet via the application.

10. The method of claim 3, wherein the recommending reintroduction comprises recommending the participant to use one or more nutrition bars designed to isolate specific ingredients within the modified diet.

11. The method of claim 1, further comprising providing a prepackaged meal plan consistent with the modified diet to the participant via the application.

12. The method of claim 2, further comprising, if improvement is shown, making a food product purchase recommendation to the participant according to the modified diet or if improvement is shown, offering a plurality of prepackaged meals compliant with the modified diet to the participant.

13. The method of claim 3, wherein the recommending reintroduction comprises recommending the participant to use one or more meal kits designed to isolate specific ingredients within the modified diet.

14. The method of claim 7, wherein the mobile computing device is a smart device.

15. The method of claim 14, wherein the smart device is a computer tablet, watch, or smart phone.

16. The method of claim 1, wherein the gastrointestinal symptoms comprise abdominal pain, bloating, distension, nausea, vomiting, heartburn, dyspepsia, or diarrhea, flatulence, cramping, or combinations thereof.

17. The method of claim 1, wherein the food sensitivity or intolerance is gluten sensitivity, lactose intolerance, fermentable oligosaccharides, disaccharides, monosaccharaides, and polyols ("FODMAPs") intolerance, a certain fat sensitivity, a certain protein sensitivity or intolerance, or a certain chemical sensitivity or intolerance.

18. The method of claim 1, wherein the FAST score accounts for the frequency, severity, and multiplicity of symptoms occurring at intervals after a culprit dietary ingestion, and compares symptoms experienced before and after the modified diet ingested by the participant.

19. The method of claim 1, further comprising:
storing the collected participant's responses;
analyzing the collected participant's responses; and
providing a variety of reports, including a daily report, heatmap report, FAST score report, or a report relating to potential dietary symptoms, based on the analysis of the responses.

20. The method of claim 1, further comprising obtaining a baseline score prior to testing the subject for food sensitivity or intolerance, prior to an elimination period, or prior to the elimination and challenge period, wherein the baseline score of the FAST score is based on the participant's normal or free range diet.

* * * * *